US010485860B2

(12) United States Patent
Bootsma et al.

(10) Patent No.: US 10,485,860 B2
(45) Date of Patent: Nov. 26, 2019

(54) VIRULENCE FACTORS OF STREPTOCOCCUS PNUEMONIAE

(71) Applicant: STICHTING KATHOLIEKE UNIVERSITEIT/RADBOUD UNIVERSITY NIJMEGEN MEDICAL CENTRE, Nijmegen (NL)

(72) Inventors: Hester Jeanette Bootsma, Utrecht (NL); Pieter Jan Burghout, Breda (NL); Peter Wilhelmus Maria Hermans, Huissen (NL); Johanna Jacoba Elisabeth Bijlsma, Groningen (NL); Oscar Paul Kuipers, Groningen (NL); Tomas Gerrit Kloosterman, Groningen (NL)

(73) Assignee: Stichting Katholieke Universiteit / Radboud University Nijmegen Medical Centre, Nijmegen (NL)

( * ) Notice: Subject to any disclaimer, the term of this patent is extended or adjusted under 35 U.S.C. 154(b) by 0 days.

(21) Appl. No.: 15/354,102

(22) Filed: Nov. 17, 2016

(65) Prior Publication Data

US 2017/0065698 A1 Mar. 9, 2017

Related U.S. Application Data

(63) Continuation of application No. 12/595,316, filed as application No. PCT/NL2008/050191 on Apr. 7, 2008, now abandoned.

(30) Foreign Application Priority Data

Apr. 12, 2007 (EP) ..................................... 07106071
Dec. 17, 2007 (EP) ..................................... 07123418

(51) Int. Cl.
| | | |
|---|---|---|
| *A61K 39/09* | (2006.01) | |
| *A61K 39/00* | (2006.01) | |
| *A61K 39/38* | (2006.01) | |
| *A61K 9/00* | (2006.01) | |
| *A61K 9/107* | (2006.01) | |
| *A61K 47/22* | (2006.01) | |

(52) U.S. Cl.
CPC .......... *A61K 39/092* (2013.01); *A61K 9/0019* (2013.01); *A61K 9/107* (2013.01); *A61K 39/09* (2013.01); *A61K 47/22* (2013.01); *A61K 2039/54* (2013.01); *A61K 2039/545* (2013.01); *A61K 2039/55594* (2013.01)

(58) Field of Classification Search
CPC ....... A61K 38/00; A61K 39/092; A61K 39/00
See application file for complete search history.

(56) References Cited

U.S. PATENT DOCUMENTS

| | | | |
|---|---|---|---|
| 6,699,703 B1 * | 3/2004 | Doucette-Stamm | ........................ A61K 31/7052 435/252.3 |
| 7,141,418 B2 | 11/2006 | Kunsch et al. | |
| 2005/0020813 A1 * | 1/2005 | Masignani | ......... C07K 14/3156 530/350 |
| 2007/0184443 A1 * | 8/2007 | Covacci | ............. C07K 14/3156 435/6.13 |

FOREIGN PATENT DOCUMENTS

| | | |
|---|---|---|
| WO | 0006737 A2 | 2/2000 |
| WO | 02/077021 | 3/2002 |
| WO | 02083855 A2 | 10/2002 |
| WO | WO 02077021 | * 10/2002 |

OTHER PUBLICATIONS https://www.cdc.gov/pneumococcal/vaccination.html.*
Van Roosmalen et al., Methods, 2006; 38: 144-149.*
Prepared Foods Nutra Solutions, Tocopherols for Preservation, Nov. 23, 2003; http://www.preparedfoods.com/articles/103674-tocopherols-for-preservation (2 pages).*
Hoskins, J. et al, "Genome of the Bacterium *Streptococcus pneumoniae* Strain 6", Journal of Bacteriology, pp. 5709-5717 (Oct. 2001).
Tettelin, H. et al, "Complete Genome Sequence of a Virulent Isolate of *Streptococcus pneumoniae*", Science, American Association for the Advancement of Science, US; vol. 293, No. 5529, pp. 498-506 (Jul. 2001).
Obert, C. et al, "Identification of a Candidate *Streptoccus pneumoniae* Core Genome and Regions of Diversity Correlated with Invasive Pneumococcal Disease", Infection and Immunity; vol. 74, No. 8, pp. 4766-4777 (Aug. 2006).
Bijlsma, J. et al, "Development of Genomic Array Footprinting for Identification of Conditionally Essential Genes in *Streptoccus pneumoniae*", Applied and Environmental Microbiology; vol. 73, No. 5, pp. 1514-1520 (Mar. 2007).

* cited by examiner

Primary Examiner — Gary B Nickol
Assistant Examiner — Lakia J Jackson-Tongue
(74) Attorney, Agent, or Firm — Reed Smith LLP; Matthew P. Frederick; Ryan P. Cox

(57) ABSTRACT

The present invention provides proteins/genes, which are essential for survival, and consequently, for virulence of *Streptococcus pneumoniae* in vivo, and thus are ideal vaccine candidates for a vaccine preparation against pneumococcal infection. Further, also antibodies against said protein(s) are included in the invention.

Figure 1:
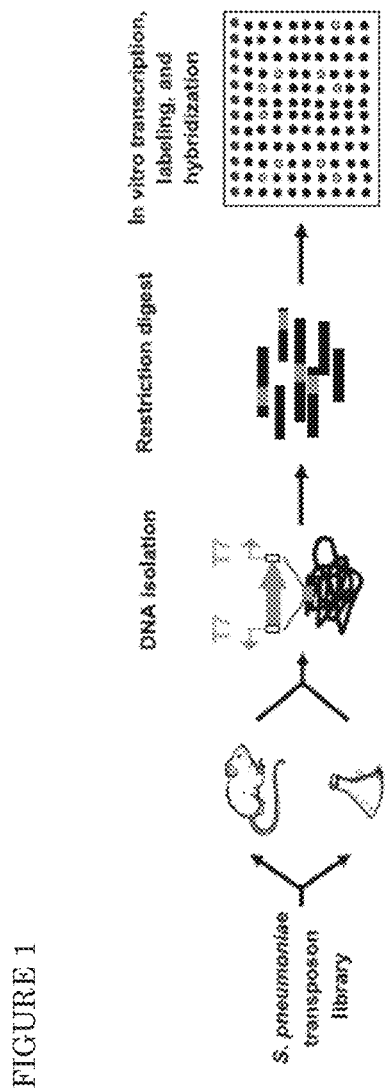

20 Claims, 4 Drawing Sheets
Specification includes a Sequence Listing.

SEQUENCE LISTING

<160> NUMBER OF SEQ ID NOS: 1

<210> SEQ ID NO 1
<211> LENGTH: 445
<212> TYPE: PRT
<213> ORGANISM: Streptococcus pneumoniae D39

<400> SEQUENCE: 1

Met Lys Lys Met Arg Lys Phe Leu Cys Leu Ala Gly Ile Ala Leu Ala
1               5                   10                  15

Ala Val Ala Leu Val Ala Cys Ser Gly Lys Lys Glu Ala Thr Thr Ser

-continued

```
                20                  25                  30
Thr Glu Pro Pro Thr Glu Leu Ser Gly Glu Ile Thr Met Trp His Ser
                    35                  40                  45
Phe Thr Gln Gly Pro Arg Leu Glu Ser Ile Gln Lys Ser Ala Asp Ala
         50                  55                  60
Phe Met Gln Lys His Pro Lys Thr Lys Ile Lys Ile Glu Thr Phe Ser
 65                  70                  75                  80
Trp Asn Asp Phe Tyr Thr Lys Trp Thr Thr Gly Leu Ala Asn Gly Asn
                 85                  90                  95
Val Pro Asp Ile Ser Thr Ala Leu Pro Asn Gln Val Met Glu Met Val
                100                 105                 110
Asn Ser Asp Ala Leu Val Pro Leu Asn Asp Ser Ile Lys Arg Ile Gly
            115                 120                 125
Gln Asp Lys Phe Asn Glu Thr Ala Leu Asn Glu Ala Lys Ile Gly Asp
        130                 135                 140
Asp Tyr Tyr Ser Val Pro Leu Tyr Ser His Ala Gln Val Met Trp Val
145                 150                 155                 160
Arg Thr Asp Leu Leu Lys Glu His Asn Ile Glu Val Pro Lys Thr Trp
                165                 170                 175
Asp Gln Leu Tyr Glu Ala Ser Lys Lys Leu Lys Glu Ala Gly Val Tyr
            180                 185                 190
Gly Leu Ser Val Pro Phe Gly Thr Asn Asp Leu Met Ala Thr Arg Phe
        195                 200                 205
Leu Asn Phe Tyr Val Arg Ser Gly Gly Ser Leu Leu Thr Lys Asp
210                 215                 220
Leu Lys Ala Asp Leu Thr Ser Gln Leu Ala Gln Asp Gly Ile Lys Tyr
225                 230                 235                 240
Trp Val Lys Leu Tyr Lys Glu Ile Ser Pro Gln Asp Ser Leu Asn Phe
                245                 250                 255
Asn Val Leu Gln Gln Ala Thr Leu Phe Tyr Gln Gly Lys Thr Ala Phe
            260                 265                 270
Asp Phe Asn Ser Gly Phe His Ile Gly Gly Ile Asn Ala Asn Ser Pro
        275                 280                 285
Gln Leu Ile Asp Ser Ile Asp Ala Tyr Pro Ile Pro Lys Ile Lys Glu
        290                 295                 300
Ser Asp Lys Asp Gln Gly Ile Glu Thr Ser Asn Ile Pro Met Val Val
305                 310                 315                 320
Trp Lys Asn Ser Lys His Pro Glu Val Ala Lys Ala Phe Leu Glu Ala
                325                 330                 335
Leu Tyr Asn Glu Glu Asp Tyr Val Lys Phe Leu Asp Ser Thr Pro Val
            340                 345                 350
Gly Met Leu Pro Thr Ile Lys Gly Ile Ser Asp Ser Ala Ala Tyr Lys
        355                 360                 365
Glu Asn Glu Thr Arg Lys Lys Phe Lys His Ala Glu Glu Val Ile Thr
        370                 375                 380
Glu Ala Val Lys Lys Gly Thr Ala Ile Gly Tyr Glu Asn Gly Pro Ser
385                 390                 395                 400
Val Gln Ala Gly Met Leu Thr Asn Gln His Ile Ile Glu Gln Met Phe
                405                 410                 415
```

```
Gln Asp Ile Ile Thr Asn Gly Thr Asp Pro Met Lys Ala Ala Lys Glu
                420                 425                 430
Ala Glu Lys Gln Leu Asn Asp Leu Phe Glu Ala Val Gln
        435                 440                 445
```

VIRULENCE FACTORS OF
STREPTOCOCCUS PNUEMONIAE

The present application is a continuation of U.S. application Ser. No. 12/595,316, filed Mar. 24, 2010, which is the United States national stage application of International Application No. PCT/NL2008/050191, filed Apr. 7, 2008, which claims the benefit of European Patent Applications Nos. 07106071.9 filed Apr. 12, 2007 and 07123418.1 filed Dec. 17, 2007. The entire contents of the applications are incorporated herein by reference herein.

SEQUENCE LISTING

The instant application contains a Sequence Listing which has been submitted electronically in ASCII format and is hereby incorporated by reference in its entirety. Said ASCII copy, created on Jan. 8, 2019, is named 09-40251-US-C_SL.txt and is 4,339 bytes in size.

FIELD OF THE INVENTION

The invention relates to the field of medicine, more especially to the field of vaccines against bacterial infections, more particularly the genus Streptococcus, more particularly the species Streptococcus pneumoniae.

BACKGROUND TO THE INVENTION

Streptococcus pneumoniae is the leading etiological agent of severe infections such as pneumonia, meningitis and sepsis. Young children, elderly and immunocompromised individuals are particularly vulnerable for pneumococcal diseases, which result in high morbidity and mortality (Hausdorff, W. P. et al., 2005, Lancet Infect. Dis. 5:83-93). The currently available vaccines against pneumococcal infections are based on serotype-specific capsular polysaccharides. These include a vaccine containing solely polysaccharides of 23 serotypes and a conjugate vaccine consisting of polysaccharides of the 7 most prevalent paediatric serotypes conjugated to an immunogenic carrier protein. The latter vaccine was introduced for the use in children under the age of 5, since their immune response to pure polysaccharides is inadequate. The introduction of this conjugate vaccine in the national vaccination program in the United States has had a major effect on invasive pneumococcal disease incidence (Whitney, C. G. et al., 2003, N. Eng. J. Med. 348:1737-1746).

Since at least 90 different polysaccharide structures are currently known within the species, polysaccharide-based vaccines only protect against a limited number of serotypes and hence, replacement by non-vaccine serotypes remains a threat for vaccine efficacy (Bogaert, D. et al., 2005, J. Clin. Microbiol. 43:74-83). Further, high production costs of the conjugate vaccines make their use in developing countries less feasible.

Treatment of Streptococcus pneumoniae infections is also impeded by the rise of strains resistant to the most commonly applied antibiotics (Levy, S. B. and Marshall, B., 2004, Nat. Med. 10:S122-S129). The development of an affordable effective vaccine against invasive pneumococcal disease in, especially, young children and elderly will have major benefits in terms of reducing disease burden and health care costs in both developed and developing countries. Immunogenic antigens of pneumococcal origin that are conserved amongst numerous serotypes would be desirable for conferring protection against infections caused by a broad range of serotypes. Much research effort is currently invested in search for pneumococcal proteins with protective potential to be included in future vaccines.

Methods searching for surface proteins of Streptococcus pneumoniae have been described (e.g. WO 98/18930), other methods have used immunological approaches to find possible antigenic determinants (WO 01/12219). On a genetic level, several methods have been used to determine which genes are needed by Streptococcus pneumoniae in the various niches it occupies in the host (conditionally essential genes) such as transcriptome analysis (Orihuela, C. J. et al., 2004, Infect. Immun. 72:4766-4777), differential fluorescence induction (Marra, A. et al., 2002, Infect. Immun. 70:1422-1433) and signature-tagged mutagenesis (Hava, D. L. and Camilli, A., 2002, Mol. Microbiol. 45:1389-1406; Lau, G. W. et al., 2001, Mol. Microbiol. 40:555-571; Polissi, A. et al., 1998, Infect. Immun. 66:5620-5629). Through these and other methods, several pneumococcal proteins have been identified and further investigated as potential vaccine candidates, such as the toxoid derivative of pneumolysin (PdB) (Briles, D. E. et al., 2003, J. Infect. Dis. 188:339-348; Ogunniyi, A. D. et al., 2000, Infect. Immun. 68:3028-3033; Ogunniyi, A. D. et al., 2001, Infect. Immun. 69:5997-6003), pneumococcal surface protein A (PspA) (Briles, D. E. et al., 2003, supra; Briles, D. E. et al., 2000, Infect. Immun. 68:796-800; Swiatlo, E. et al., 2003, Infect. Immun. 2003, 71:7149-7153; Wu, H. Y. et al., 1997, J. Infect. Dis. 175:839-846), pneumococcal surface adhesion A (PsaA) (Briles, D. E. et al., 2000, supra), choline binding protein A (CbpA) (Ogunniyi, A. D. et al., 2000, supra), BVH-3 (Hamel, J. et al., 2004, Infect. Immun. 72:2659-2670), PiuA and PiaA (Brown, J. S. et al., 2001, Infect. Immun. 69:6702-6706), pneumococcal protective protein A (PppA) (Green, B. A. et al., 2005, Infect. Immun. 73:981-989), putative proteinase maturation protein A (PpmA) (Adrian, P. V. et al., 2004, Vaccine 22:2737-2742; Overweg, K. et al., 2000, Infect. Immun. 68:4180-4188), IgA1 protease (IgAlp) (Weiser, J. N. et al., 2003, Proc. Natl. Acad. Sci. USA 100:4215-4220) and the streptococcal lipoprotein rotamase A (SlrA) (Adrian, P. V. et al. supra).

Yet, there is still need for new vaccine candidates.

SUMMARY OF THE INVENTION

The inventors now have found several proteins/genes of Streptococcus pneumoniae which are essential for the virulence of the pathogen, and which thus would be applicable in a vaccine for combating pneumococcal infections.

Accordingly, the invention comprises a vaccine formulation providing protection against pneumococcal infection in a subject, said formulation comprising an effective amount of a protein encoded by a gene listed in Table 1, Table 2, Table 3, and/or Table 4 or a functional homologue or an immunogenic part thereof together with at least one of a pharmaceutically acceptable diluent, carrier, excipient or adjuvant therefore. Preferably said immunogenic part is antigenic determinant of said pathogen. The protein of said formulation is preferably encoded by a gene listed in Table 5, or alternatively said protein is encoded by a gene listed in Table 1A, Table 1B, Table 2A, Table 2B, Table 3A, Table 3B, Table 4A, and/or Table 4B, while most preferably said protein is encoded by a gene listed in two or more of Table 1A or Table 1B, Table 2A or Table 2B, Table 3A or Table 3B, and Table 4A or Table 4B.

Further comprised in the invention is a formulation according to the above formulations, wherein said formulation provides protections against pneumonia, meningitis, otitis media and/or sepsis caused by *Streptococcus pneumoniae*.

In another embodiment, the invention comprises a protein encoded by a gene listed in Table 1, 2, 3, and/or 4 or an immunogenic part thereof, for use as a vaccine.

In another embodiment the invention comprises an antibody against a protein encoded by a gene listed in Table 1, 2, 3, and/or 4 or fragment thereof, preferably a humanized antibody or fragment thereof. Preferably said antibody or fragment thereof, preferably a humanized antibody or fragment thereof is for use as a medicament for the prophylactic or therapeutic treatment of a pneumococcal infection in a subject.

In yet another embodiment the invention comprises the use of said antibody or fragment thereof, preferably said humanized antibody or fragment thereof for the manufacture of a medicament for the prophylactic or therapeutic treatment of a pneumococcal infection in a subject.

Also comprised in the invention is a pharmaceutical composition comprising said antibody or fragment thereof, preferably said humanized antibody or fragment thereof, and a pharmaceutically acceptable carrier.

Further comprised in the invention is a method for prophylactic or therapeutic treatment of a pneumococcal infection in a subject comprising administering to a subject in need of such treatment an effective amount of a vaccine formulation as defined above and/or an effective amount of a pharmaceutical composition as defined above.

In another embodiment the invention comprises a method for preparing a pneumococcal vaccine formulation, the said method comprising bringing into association, an effective amount of a protein encoded by a gene listed in Table 1, Table 2, Table 3, and/or Table 4 or an immunogenic part thereof and at least one of a pharmaceutically acceptable diluent, carrier, excipient or adjuvant therefore. Preferably, said method comprises bringing into association, an effective amount of an antibody, preferably a humanized antibody, or fragment thereof, as described above and a pharmaceutically acceptable carrier.

LEGENDS TO THE FIGURES

FIG. 1 shows a schematic representation of the GAF procedure. A large *Streptococcus pneumoniae* transposon library is grown under nonselective and selective conditions. Subsequently, chromosomal DNA containing transposon (grey rectangle) with outward-facing T7 RNA polymerase promoters (arrow with T7) is isolated from each population. The DNA is digested, and the DNA adjacent to the transposon insertion site is amplified using in vitro transcription with T7 RNA polymerase. The RNA is used in standard procedures for microarray probe synthesis. Co-hybridization of probes derived from non-selective and selective conditions to a microarray will reveal which genes were disrupted in the mutants that disappeared during selection: only material derived from the nonselective condition will hybridise to those spots (grey spots).

Figure 2A:
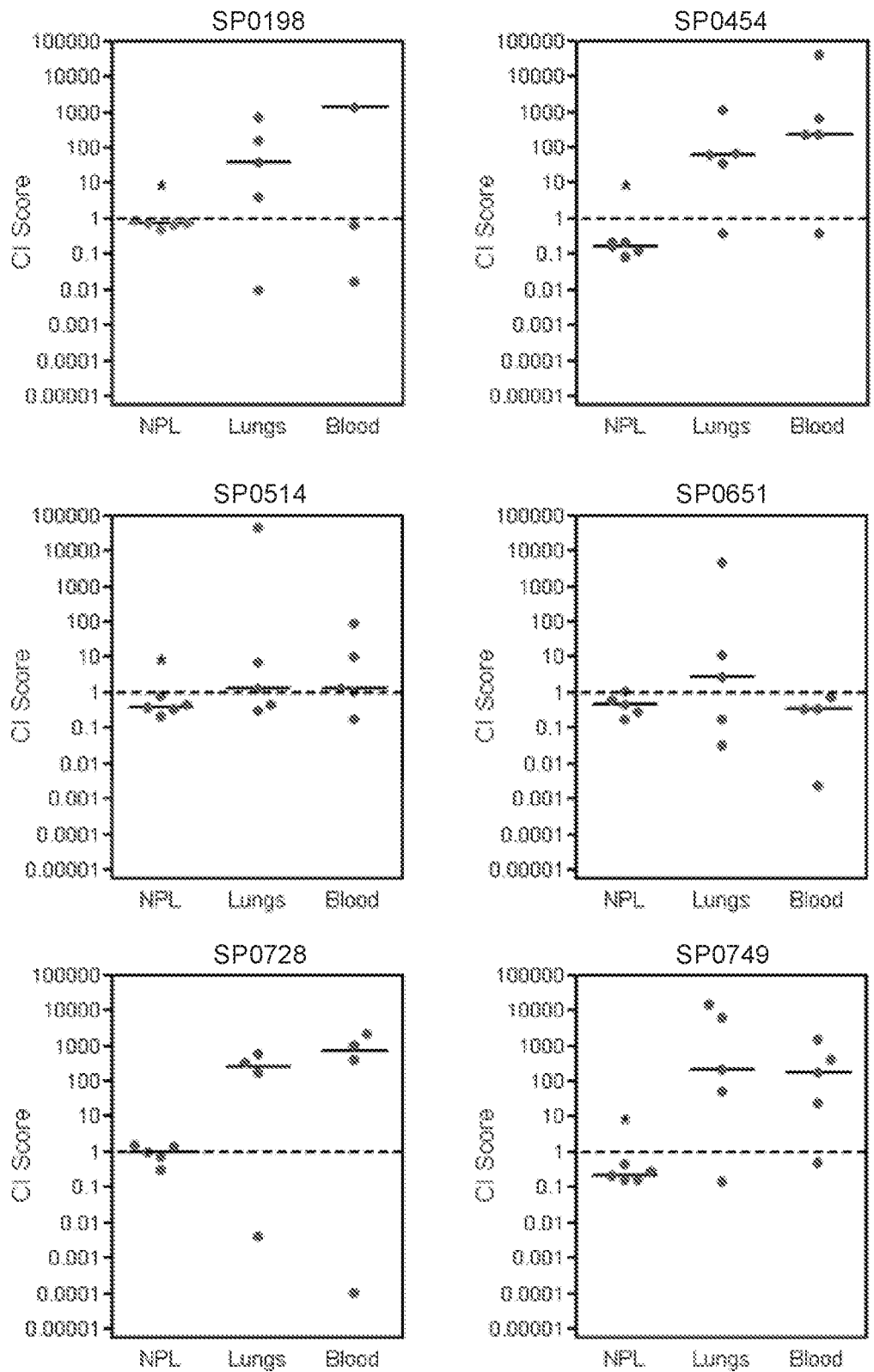
Figure 2B:
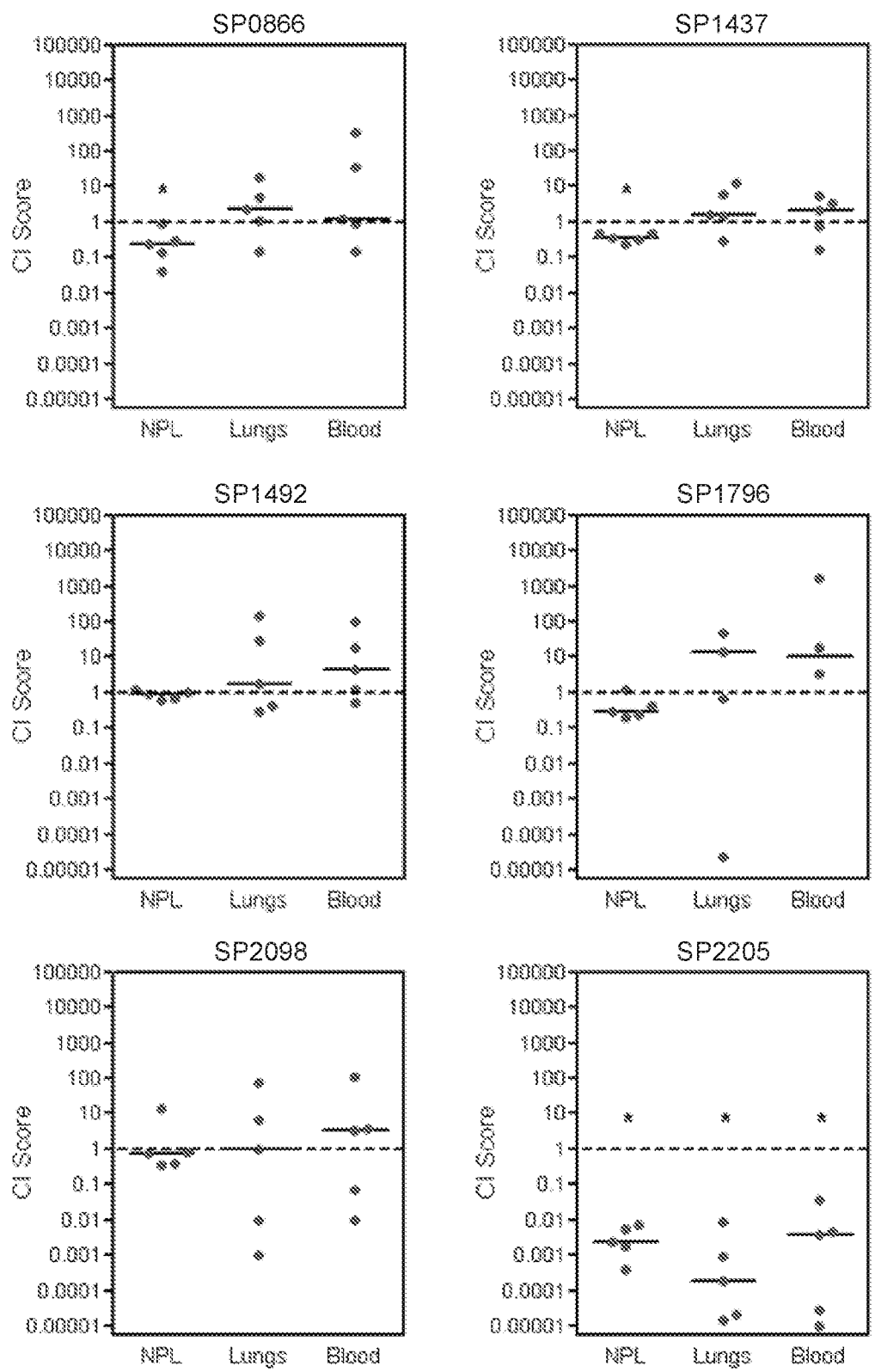

FIG. 2A and 2B. show the validation of identified targets in the pneumonia model. Shown are the CI scores obtained after co-infection of mice with a 1:1 mixture of streptomycin-resistant TIGR4 and a particular mutant. The genes that were deleted in these mutants are indicated above each graph, the compartment sampled below each graph. Each dot represents one mouse. Median CI scores are indicated by horizontal bars. Statistical significance with a P<0.05 is depicted with an *.

Figure 3:
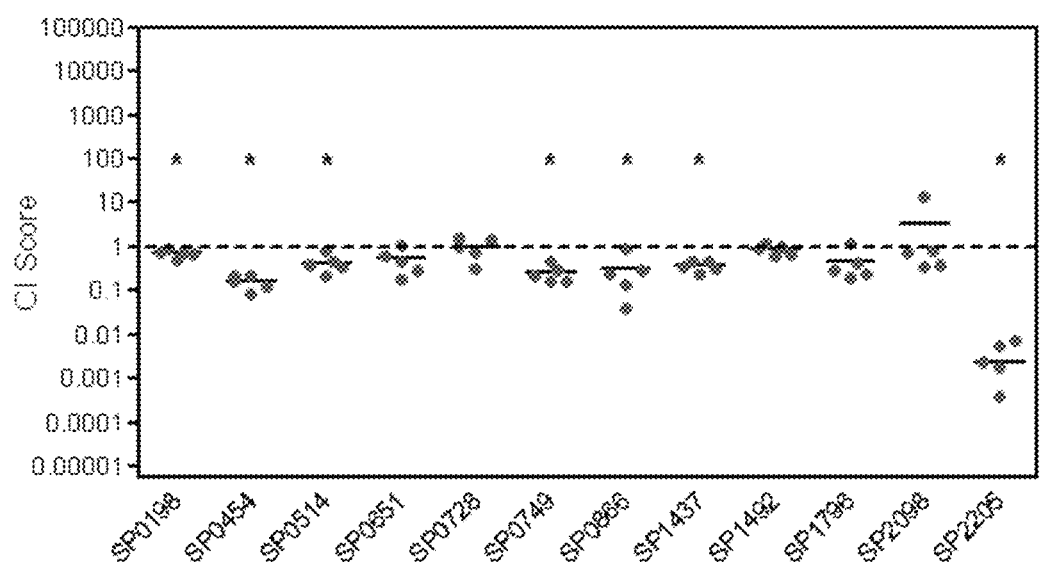

FIG. 3. shows the validation of identified targets in the pneumonia model, summarizing the results of the nasopharynx (NPL). Shown are the CI scores obtained in the NPL after co-infection of mice with a 1:1 mixture of streptomycin-resistant TIGR4 and a particular mutant. The genes that were deleted in these mutants are indicated below the graph. Each dot represents one mouse. Median CI scores are indicated by horizontal bars. Statistical significance with a P<0.05 is depicted with an *.

DETAILED DESCRIPTION

A "virulence factor" is referred to herein as a property of a pathogen that allows it to colonize and survive in the host, and consequently to cause disease. Virulence factors may distinguish a pathogenic micro-organism from otherwise identical non-pathogenic micro-organisms by allowing pathogens to invade, adhere to, and/or colonize a host, and then harm the host, as for an organism to be pathogenic it must be able to invade a host, multiply in the host, evade host defences, and harm the host in some way. As used herein the gene product of the genes of Table 1, 2, 3, and 4 are virulence factors.

The terms "invade" and "invasion" refer to the growing of infections into tissues, i.e., through and then beneath epithelial tissues, in particular it encompasses to the process of passage of mucosal tissue, either in the nasopharyngeal tissue or in the lungs, to the lymph fluid, the blood and/or the meningi. Thus, it encompasses both nasopharyngeal colonization and dissemination to the blood/meningi.

The term "functional fragment" refers to a shortened version of the protein, which is a functional variant or functional derivative. A "functional variant" or a "functional derivative" of a protein is a protein the amino acid sequence of which can be derived from the amino acid sequence of the original protein by the substitution, deletion and/or addition of one or more amino acid residues in a way that, in spite of the change in the amino acid sequence, the functional variant retains at least a part of at least one of the biological activities of the original protein that is detectable for a person skilled in the art. A functional variant is generally at least 60% homologous (preferably the amino acid sequence is at least 60% identical), advantageously at least 70% homologous and even more advantageously at least 80 or 90% homologous to the protein from which it can be derived. A functional variant may also be any functional part of a protein; the function in the present case being particularly but not exclusively essential activity for nasopharyngeal or blood colonization. "Functional" as used herein means functional in *Streptococcus pneumoniae* bacteria and capable of eliciting antibodies which give protection against disease caused by said bacteria.

The expression "conservative substitutions" as used with respect to amino acids relates to the substitution of a given amino acid by an amino acid having physicochemical characteristics in the same class. Thus where an amino acid of the protein encoded by the genes listed in Tables 1, 2, 3, and 4 has a hydrophobic characterising group, a conservative substitution replaces it by another amino acid also having a hydrophobic characterising group; other such classes are those where the characterising group is hydrophilic, cationic, anionic or contains a thiol or thioether. Such substitutions are well known to those of ordinary skill in the art, i.e. see U.S. Pat. No. 5,380,712. Conservative amino acid substitutions may be made, for example within the group of aliphatic non-polar amino acids (Gly, Ala, Pro, Ile, Leu, Val), the group of polar uncharged amino acids (Cys, Ser, Thr, Met, Asn, Gln), the group of polar charged amino acids (Asp, Glu, Lys, Arg) or the group of aromatic amino acids (His, Phe, Tyr, Trp).

The term "immunogenic part" includes reference to any part of a protein encoded by the genes listed in Tables 1, 2, 3, and 4, or a functional homologue or functional fragment thereof, which is capable of eliciting an immune response in a mammal. Said immunogenic part preferably corresponds to an antigenic determinant of said pathogen.

As used herein, the term "antigen" refers to a molecule capable of being bound by an antibody or a T cell receptor (TCR) if presented by molecules of the major histocompatibility complex (MHC). The term "antigen", as used herein, also encompasses T-cell epitopes. A T-cell epitope is recognized by a T-cell receptor in the context of a MHC class I, present on all cells of the body except erythrocytes, or class II, present on immune cells and in particular antigen presenting cells. This recognition event leads to activation of T-cells and subsequent effector mechanisms such as proliferation of the T-cells, cytokine secretion, perforin secretion etc. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a T-Helper cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens. Antigens, as used herein, include infectious disease antigens, more especially antigens of *Streptococcus pneumoniae*, more preferable antigens derived from the proteins encoded by the genes listed in Tables 1, 2, 3, and 4 and fragments and derivatives thereof. Furthermore, antigens used for the present invention can be peptides, proteins, domains, or lipids, especially those lipids that are associated to the proteins encoded by the genes listed in Tables 1, 2, 3, and 4 as lipoproteins.

As used herein, the term "antigenic determinant" is meant to refer to that portion of an antigen that is specifically recognized by either B- or T-lymphocytes. B-lymphocytes respond to foreign antigenic determinants via antibody production, whereas T-lymphocytes are the mediator of cellular immunity. Thus, antigenic determinants or epitopes are those parts of an antigen that are recognized by antibodies, or in the context of an MHC, by T-cell receptors. An antigenic determinant may contain one or more epitopes. Epitopes may be present on the intracellular (inside), transmembrane spanning (transmembrane), as well as extracellular (outside) regions of a protein molecule. It is expected that antigenic determinants are associated with in particular those regions of the surface proteins encoded by the genes listed in Tables 1A, 1B, 2A, 2B, 3A, 3B, 4A, and 4B which are on the outside of the cytoplasmic membrane of the bacteria. These regions can be predicted from the sequences as provided, by using for instance one of the software programs SignalP3.0, PSORTb or TMHMM, e.g. version 2.0c, which provides a method for prediction transmembrane helices based on a hidden Markov model.

The term "prophylactic or therapeutic treatment of an infection by *Streptococcus pneumoniae*" or "prophylactic or therapeutic treatment of a pneumococcal infection" refers to both prophylactic or therapeutic treatments wherein virulence of the pathogen is blocked or diminished, but also to treatments wherein antibodies against any of the proteins encoded by the genes listed in Table 1, 2, 3, or 4 recognize the bacteria and will protect the host against infection, either directly through immune clearance, or indirectly by blocking the activity of the protein, thereby inhibiting the growth of the bacteria. Also, the term refers to blocking the function of any of the proteins encoded by the genes listed in Tables 1, 2, 3, and 4 in vivo thereby reducing the adhesion abilities of the pathogen with a concomitant reduction in colonization and invasion capabilities. The term thus includes inducing immune responses in subjects using vaccine formulations of the invention, as well as inhibiting growth of the pathogen in vivo by using antibodies of the present invention as an active compound in a pharmaceutical composition administered to the subject. Also included is the inhibition of the virulence and/or growth of the bacteria by treatment with antibiotics.

The term "antibody" refers to molecules which are capable of binding an epitope or antigenic determinant and includes reference to antigen binding forms of antibodies (e. g., Fab, F(ab)2). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i. e., comprising constant and variable regions from different species), humanized antibodies (i. e., comprising a complementarity determining region (CDR) from a non-human source) and heteroconjugate antibodies (e. g., bispecific antibodies). The antibody can be monoclonal or polyclonal and can be prepared by techniques that are well known in the art such as immunization of a host and collection of sera (polyclonal) (see, e.g., Parker, Radioimmunoassay of Biologically Active Compounds, Prentice-Hall (Englewood Cliffs, N.J., U.S., 1976), Butler, *J. Immunol. Meth.* 7, 1-24 (1975); Broughton and Strong, *Clin. Chem.* 22, 726-732 (1976); and Playfair, et al., *Br. Med. Bull.* 30, 24-31 (1974)) or by preparing continuous hybrid cell lines and collecting the secreted protein (monoclonal) (see, e.g., Kohler et al in *Nature* 256, 495-497 (1975) and *Eur. J. Immunol.* 6, 511-519 (1976); by Milstein et al. *Nature* 266, 550-552 (1977); and by Walsh *Nature* 266, 495 (1977)) or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular molecule is maintained.

As used herein, the term "monoclonal antibody" refers to an antibody composition having a homogeneous antibody population. The term is not limited regarding the species or source of the antibody, nor is it intended to be limited by the manner in which it is made. The term encompasses whole immunoglobulins as well as fragments such as Fab, F(ab')2, Fv, and others, such as CDR fragments, which retain the antigen binding function of the antibody. Monoclonal antibodies of any mammalian species can be used in this invention. In practice, however, the antibodies will typically be of rat or murine origin because of the availability of rat or murine cell lines for use in making the required hybrid cell lines or hybridomas to produce monoclonal antibodies.

As used herein, the term "humanized monoclonal antibodies" means that at least a portion of the exposed amino acids in the framework regions of the antibody (or fragment), which do not match with the corresponding amino acids in the most homologous human counterparts, are changed, such as by site directed mutagenesis of the DNA encoding the antibody. Because these exposed amino acids are on the surface of the molecule, this technique is called "resurfacing." Moreover, because the amino acids on the surface of the molecule are the ones most likely to give rise to an immune response, this resurfacing decreases the immunogenicity of the monoclonal antibody when administered to a species whose cell line was not used to generate the antibody, such as a human. The term "humanized monoclonal antibody" also includes chimeric antibody wherein the light and heavy variable regions of a monoclonal antibody generated by a hybridoma from a non-human cell line are each attached, via recombinant technology, to one human light chain constant region and at least one heavy chain constant region, respectively. The preparation of such chimeric (i. e., humanized) antibodies are well known in the art.

The term "specifically recognizing", includes reference to a binding reaction between an antibody and a protein having an epitope recognized by the antigen binding site of the antibody. This binding reaction is determinative of the presence of a protein having the recognized epitope amongst the presence of a heterogeneous population of proteins and other biologics. Specific binding to an antibody under such conditions may require an antibody that is selected for its specificity for a particular protein. For example, antibodies raised to the proteins encoded by the genes listed in Tables 1, 2, 3, and 4 of the present invention can be selected to obtain antibodies specifically recognizing said proteins. The proteins used as immunogens can be in native conformation or denatured so as to provide a linear epitope. A variety of immunoassay formats may be used to select antibodies specifically recognizing a particular protein (or other analyte). For example, solid-phase ELISA immunoassays are routinely used to select monoclonal antibodies specifically immunoreactive with a protein. See Harlow and Lane, Antibodies, A Laboratory Manual, Cold Spring Harbor Publications, New York (1988), for a description of immunoassay formats and conditions that can be used to determine selective reactivity.

A "subject" as referred to herein is meant to include mammals and other animals, wherein mammals include for example, humans, apes, monkeys, horses, cattle, pigs, goats, dogs, cats, rats, mice, and sheep. The term "non-human animal" is meant to disclaim humans. Preferably in the present invention, the subject is a human, more preferably a child or an elderly person.

The virulence proteins/genes of the present invention have been identified by genomic array footprinting (GAF), which is a high-throughput method to identify conditionally essential gene in Streptococcus pneumoniae by using a combination of random transposon mutagenesis and microarray technology (see Bijlsma, J. J. E. et al., 2007, Appl. Environm. Microbiol. 73(5):1514-1524). GAF detects the transposon insertion sites in a mutant library by amplifying and labelling the chromosomal DNA adjacent to the transposon and subsequent hybridisation of these probes to a microarray. Identification of transposon insertion sites in mutants that have disappeared from the library due to selection, which represent conditionally essential genes, is achieved by differential hybridisation of the probes generated from the library grown under two conditions to an array (FIG. 1). For the detection of essential genes for nasopharyngeal colonization and/or dissemination to and/or survival in the blood, mutant libraries of Streptococcus pneumoniae (prepared as described in the experimental part) were used to infect mice in a murine pneumonia model of infection. For specific detection of essential genes for nasopharyngeal colonization, mutant libraries of Streptococcus pneumoniae (prepared as described in the experimental part) were used to infect mice in a murine colonization model of infection. For specific detection of essential genes for survival in the blood, mutant libraries of Streptococcus pneumoniae (prepared as described in the experimental part) were used to infect mice in a murine bacteraemia model of infection. After challenge mutants were identified that had disappeared from the nasopharyngeal lavage and/or blood samples taken from the mice, and the disrupted genes of these mutants were identified.

The genes found to be essential for nasopharyngeal colonization in the pneumonia model are provided in Table 1. Table 1A lists the genes which are predicted to be located at the surface based on their sequence (using various prediction servers, such as SignalP3.0 (http://www.cbs.dtu.dk/services/SignalP), and PSORTb (http://www.psort.org). Table 1B lists the genes which are predicted to be surface localised, based on the following criteria:

one to three predicted transmembrane helices (determined using TMHMM (http://www.cbs.dtu.dk/services/TMHMM)); or components IIC and IID of PTS systems; or capsule gene loci.

Table 1C lists the genes which are predicted to be localised in the cytoplasma, or which could not be used in prediction servers, because the ORF was annotated as pseudogene or frame-shifted.

The genes found to be essential for dissemination to and/or survival in the blood in the pneumonia model are listed in Tables 2A-2C on the same criteria as for Table 1.

The genes found to be essential for nasopharyngeal colonization in the colonization model are provided in Table 3A-3C on the same criteria as for Table 1.

The genes found to be essential for survival in the blood in the bacteraemia model are listed in Tables 4A-4C on the same criteria as for Table 1.

The surface-localised proteins of the genes of Table 1, 2, 3, and Table 4 are especially preferred as a vaccine component according to the present invention.

Table 5 lists the genes which appear in at least two of Tables 1, 2, 3, and 4 and which are especially preferred in the present invention.

Next to the genes listed in Tables 1, 2, 3, and 4, more genes (listed in Table 6) have been identified in the current experimental set-up. These genes/proteins of Table 6 have been identified earlier as genes/proteins which would be suitable as vaccine candidates for Streptococcus pneumoniae. The fact that these genes were found in our experiments emphasizes the usefulness of the methodology for finding potential vaccine candidates.

TABLE 1A

Conditionally essential *Streptococcus pneumoniae* genes identified in nasopharyngeal lavage in the pneumonia model that encode a predicted surface-localised protein. Locus indicates the gene number assigned by TIGR-CMG annotation (Tettelin H. et al., 2001, Science. 293: 498-506; TIGR Comprehensive Microbial Resource database http://cmr.tigr.org/tigr-script/CMR/CmrHomePage.cgi).

| Locus | Annotation | Gene | Mainrole |
|---|---|---|---|
| SP0042 | competence factor transporting ATP-binding/permease protein ComA | comA | Cellular processes |
| SP0112 | amino acid ABC transporter, periplasmic AA-binding protein, putative | | Transport and binding proteins |
| SP0651 | conserved hypothetical protein | | Hypothetical proteins-Conserved |
| SP0749 | branched-chain amino acid ABC transporter, AA-binding protein | livJ | Transport and binding proteins |
| SP0769 | VanZF-related protein | | Unknown function |
| SP1002 | adhesion lipoprotein | lmb | Cellular processes |
| SP1437 | conserved domain protein | | Hypothetical proteins-Domain |
| SP1492 | cell wall surface anchor family protein | | Cell envelope |
| SP1624 | acyltransferase family protein | | Unknown function |
| SP1690 | ABC transporter, substrate-binding protein (aa sequaence SEQ ID NO: 1) | | Transport and binding proteins |
| SP1826 | ABC transporter, substrate-binding protein | | Transport and binding proteins |
| SP1955 | hypothetical protein | | Hypothetical proteins |
| SP2010 | penicillin-binding protein 2A | pbp2A | Cell envelope |
| SP2050 | competence protein CgID | cgID | Cellular processes |
| SP2084 | phosphate ABC transporter, phosphate-binding protein | pstS | Transport and binding proteins |
| SP2147 | hypothetical protein | | Hypothetical proteins |
| SP2197 | ABC transporter, substrate-binding protein, putative | | Transport and binding proteins |

TABLE 1B

Conditionally essential *Streptococcus pneumoniae* genes identified in nasopharyngeal lavage in the pneumonia model, which encode a predicted surface-localised protein.

| Locus | Annotation | Gene | Mainrole |
|---|---|---|---|
| SP0282 | PTS system, mannose-specific IID component | | Transport and binding proteins |
| SP0283 | PTS system, mannose-specific IIC component | manM | Transport and binding proteins |
| SP0514 | hypothetical protein | | Hypothetical proteins |
| SP0866 | hypothetical protein | | Hypothetical proteins |
| SP1368 | psr protein | | Unknown function |
| SP1617 | PTS system, IIC component | | Transport and binding proteins |
| SP2038 | PTS system, membrane component, putative | | Transport and binding proteins |
| SP2205 | DHH subfamily 1 protein | | Unknown function |

TABLE 1C

Conditionally essential *Streptococcus pneumoniae* genes identified in nasopharyngeal lavage in the pneumonia model, which encode a predicted cytoplasm-localised protein.

| SP nr. | Annotation | Gene | Mainrole |
|---|---|---|---|
| SP0021 | deoxyuridine 5triphosphate nucleotidohydrolase, putative | | Purines, pyrimidines, etc |
| SP0051 | phosphoribosylamine--glycine ligase | purD | Purines, pyrimidines, etc |
| SP0058 | transcriptional regulator, GntR family | | Regulatory functions |
| SP0061 | PTS system, IIB component | | Transport and binding proteins |
| SP0106 | L-serine dehydratase, iron-sulfur-dependent, beta subunit | sdhB | Energy metabolism |
| SP0113 | argininosuccinate synthase, truncation | argG | Disrupted reading frame |
| SP0116 | hypothetical protein | | Hypothetical proteins |
| SP0152 | ABC transporter, permease protein, putative | | Transport and binding proteins |
| SP0168 | macrolide efflux protein, putative | | Transport and binding proteins |
| SP0181 | conserved hypothetical protein | | Hypothetical proteins-Conserved |
| SP0182 | MccC family protein | | Unknown function |
| SP0200 | competence-induced protein Ccs4 | ccs4 | Unknown function |
| SP0202 | anaerobic ribonucleoside-triphosphate reductase | nrdD | Purines, pyrimidines, etc |
| SP0206 | hypothetical protein | | Hypothetical proteins |
| SP0245 | pyruvate formate-lyase-activating enzyme, putative | | Energy metabolism |
| SP0255 | acetyltransferase, GNAT family | | Unknown function |
| SP0259 | Holliday junction DNA helicase RuvB | ruvB | DNA metabolism |
| SP0263 | eep protein | eep | Cellular processes |
| SP0280 | ribosomal small subunit pseudouridine synthase A | rsuA-1 | Protein synthesis |
| SP0302 | conserved domain protein | | Hypothetical proteins-Domain |
| SP0317 | 4-hydroxy-2-oxoglutarate aldolase/2-deydro-3-deoxyphosphogluconate aldolase | | Energy metabolism |

TABLE 1C-continued

Conditionally essential *Streptococcus pneumoniae* genes
identified in nasopharyngeal lavage in the pneumonia model, which encode a
predicted cytoplasm-localised protein.

| SP nr. | Annotation | Gene | Mainrole |
|---|---|---|---|
| SP0318 | carbohydrate kinase, PfkB family | | Energy metabolism |
| SP0321 | PTS system, IIA component | | Transport and binding proteins |
| SP0333 | transcriptional regulator, putative | | Regulatory functions |
| SP0340 | autoinducer-2 production protein | luxS | Cellular processes |
| SP0404 | hypothetical protein | | Hypothetical proteins |
| SP0409 | conserved hypothetical protein | | Hypothetical proteins-Conserved |
| SP0442 | conserved hypothetical protein | | Hypothetical proteins-Conserved |
| SP0446 | acetolactate synthase, small subunit | ilvN | Amino acid biosynthesis |
| SP0453 | amino acid ABC transporter, AA-binding protein/permease protein | | Transport and binding proteins |
| SP0473 | ROK family protein | | Regulatory functions |
| SP0481 | conserved hypothetical protein | | Hypothetical proteins-Conserved |
| SP0482 | conserved hypothetical protein | | Hypothetical proteins-Conserved |
| SP0488 | conserved hypothetical protein | | Hypothetical proteins-Conserved |
| SP0489 | PAP2 family protein | | Unknown function |
| SP0491 | hypothetical protein | | Hypothetical proteins |
| SP0515 | heat-inducible transcription repressor HrcA | hrcA | Regulatory functions |
| SP0521 | HIT family protein | | Unknown function |
| SP0525 | blpS protein | blpS | Unknown function |
| SP0557 | ribosome-binding factor A | rbfA | Transcription |
| SP0565 | conserved domain protein | | Hypothetical proteins-Domain |
| SP0585 | 5-methyltetrahydropteroyltriglutamate--homocysteine methyltransferase | metE | Amino acid biosynthesis |
| SP0592 | conserved hypothetical protein | | Hypothetical proteins-Conserved |
| SP0611 | single-stranded-DNA-specific exonuclease RecJ | recJ | DNA metabolism |
| SP0615 | beta-lactam resistance factor | fibA | Cell envelope |
| SP0634 | conserved domain protein | | Hypothetical proteins-Domain |
| SP0676 | transcriptional regulator, putative | | Regulatory functions |
| SP0687 | ABC transporter, ATP-binding protein | | Transport and binding proteins |
| SP0695 | HesA/MoeB/ThiF family protein | | Unknown function |
| SP0696 | hypothetical protein | | Hypothetical proteins |
| SP0705 | hypothetical protein | | Hypothetical proteins |
| SP0736 | mannose-6-phosphate isomerase | manA | Energy metabolism |
| SP0743 | transcriptional regulator, TetR family | | Regulatory functions |
| SP0744 | cytidine and deoxycytidylate deaminase family protein | | Unknown function |
| SP0745 | uracil phosphoribosyltransferase | upp | Purines, pyrimidines, etc |
| SP0748 | conserved hypothetical protein | | Hypothetical proteins-Conserved |
| SP0750 | branched-chain amino acid ABC transporter, permease protein | livH | Transport and binding proteins |
| SP0751 | branched-chain amino acid ABC transporter, permease protein | livM | Transport and binding proteins |
| SP0752 | branched-chain amino acid ABC transporter, ATP-binding protein | livG | Transport and binding proteins |
| SP0753 | branched-chain amino acid ABC transporter, ATP-binding protein | livF | Transport and binding proteins |
| SP0754 | acetoin utilization protein AcuB, putative | acuB | Energy metabolism |
| SP0768 | conserved hypothetical protein | | Hypothetical proteins-Conserved |
| SP0777 | hypothetical protein | | Hypothetical proteins |
| SP0786 | ABC transporter, ATP-binding protein | | Transport and binding proteins |
| SP0815 | hypothetical protein | | Hypothetical proteins |
| SP0816 | hypothetical protein | | Hypothetical proteins |
| SP0817 | MutT/nudix family protein | | DNA metabolism |
| SP0828 | ribose 5-phosphate isomerase | rpiA | Energy metabolism |
| SP0830 | hypothetical protein | | Hypothetical proteins |
| SP0831 | purine nucleoside phosphorylase, family 2 | deoD | Purines, pyrimidines, etc |
| SP0848 | sugar ABC transporter, permease protein, putative | | Transport and binding proteins |
| SP0876 | 1-phosphofructokinase, putative | | Energy metabolism |
| SP0881 | thiazole biosynthesis protein ThiI | thiI | Biosynthesis of cofactors, etc |
| SP0882 | conserved hypothetical protein | | Hypothetical proteins-Conserved |
| SP0893 | transcriptional repressor, putative | | Regulatory functions |
| SP0921 | conserved hypothetical protein | | Hypothetical proteins-Conserved |
| SP0950 | acetyltransferase, GNAT family | | Unknown function |
| SP0962 | lactoylglutathione lyase | gloA | Energy metabolism |
| SP0972 | multi-drug resistance efflux pump | pmrA | Transport and binding proteins |
| SP1011 | GtrA family protein | | Unknown function |
| SP1025 | hypothetical protein | | Hypothetical proteins |
| SP1039 | hypothetical protein | | Hypothetical proteins |
| SP1052 | phosphoesterase, putative | | Unknown function |
| SP1053 | conserved domain protein | | Hypothetical proteins-Domain |

TABLE 1C-continued

Conditionally essential *Streptococcus pneumoniae* genes
identified in nasopharyngeal lavage in the pneumonia model, which encode a
predicted cytoplasm-localised protein.

| SP nr. | Annotation | Gene | Mainrole |
|---|---|---|---|
| SP1054 | Tn5252, Orf 10 protein | | Mobile and extrachromosomal element |
| SP1055 | Tn5252, Orf 9 protein | | Mobile and extrachromosomal element |
| SP1061 | protein kinase, putative | | Regulatory functions |
| SP1096 | conserved hypothetical protein | | Hypothetical proteins-Conserved |
| SP1104 | hypothetical protein | | Cell envelope |
| SP1119 | glyceraldehyde-3-phosphate dehydrogenase, NADP-dependent | gapN | Energy metabolism |
| SP1136 | conserved domain protein | | Hypothetical proteins-Domain |
| SP1167 | dihydroorotase, multifunctional complex type | pyrC | Purines, pyrimidines, etc |
| SP1177 | phosphocarrier protein HPr | ptsH | Transport and binding proteins |
| SP1190 | tagatose 1,6-diphosphate aldolase | lacD | Energy metabolism |
| SP1222 | type II restriction endonuclease, putative | | DNA metabolism |
| SP1235 | MutT/nudix family protein | | DNA metabolism |
| SP1245 | Cof family protein | | Unknown function |
| SP1280 | conserved hypothetical protein | | Hypothetical proteins-Conserved |
| SP1289 | hypothetical protein | | Hypothetical proteins |
| SP1298 | DHH subfamily 1 protein | | Unknown function |
| SP1299 | ribosomal protein L31 | rpmE | Protein synthesis |
| SP1320 | v-type sodium ATP synthase, subunit E | ntpE | Transport and binding proteins |
| SP1333 | hypothetical protein | | Hypothetical proteins |
| SP1341 | ABC transporter, ATP-binding protein | | Transport and binding proteins |
| SP1370 | shikimate kinase | aroK | Amino acid biosynthesis |
| SP1371 | 3-phosphoshikimate 1-carboxyvinyltransferase | aroA | Amino acid biosynthesis |
| SP1375 | 3-dehydroquinate synthase | aroB | Amino acid biosynthesis |
| SP1376 | shikimate 5-dehydrogenase | aroE | Amino acid biosynthesis |
| SP1393 | conserved hypothetical protein | | Hypothetical proteins-Conserved |
| SP1397 | phosphate ABC transporter, ATP-binding protein, putative | | Transport and binding proteins |
| SP1422 | hypothetical protein | | Hypothetical proteins |
| SP1429 | peptidase, U32 family | | Protein fate |
| SP1449 | cppA protein | cppA | Unknown function |
| SP1463 | methylated-DNA--protein-cysteine S-methyltransferase | ogt | DNA metabolism |
| SP1465 | hypothetical protein | | Hypothetical proteins |
| SP1467 | conserved hypothetical protein | | Hypothetical proteins-Conserved |
| SP1468 | pyridoxine biosynthesis protein | | Biosynthesis of cofactors, etc |
| SP1471 | oxidoreductase, putative | | Unknown function |
| SP1478 | oxidoreductase, aldo/keto reductase family | | Unknown function |
| SP1506 | conserved hypothetical protein | | Hypothetical proteins-Conserved |
| SP1519 | acetyltransferase, GNAT family | | Unknown function |
| SP1537 | general stress protein 13, putative | | Cellular processes |
| SP1562 | hypothetical protein | | Hypothetical proteins |
| SP1563 | pyridine nucleotide-disulphide oxidoreductase family protein | | Unknown function |
| SP1567 | endoribonuclease L-PSP | | Transcription |
| SP1568 | GTP-binding protein | | Unknown function |
| SP1578 | methyltransferase, putative | | Unknown function |
| SP1601 | conserved hypothetical protein | | Hypothetical proteins-Conserved |
| SP1602 | phnA protein | phnA | Transport and binding proteins |
| SP1609 | conserved hypothetical protein | | Hypothetical proteins-Conserved |
| SP1621 | transcription antiterminator BgIG family protein, authentic frameshift | | Transcription |
| SP1625 | cadmium resistance transporter, putative | | Transport and binding proteins |
| SP1626 | ribosomal protein S15 | rpsO | Protein synthesis |
| SP1642 | hypothetical protein | | Hypothetical proteins |
| SP1643 | hypothetical protein | | Hypothetical proteins |
| SP1685 | conserved hypothetical protein | | Hypothetical proteins-Conserved |
| SP1686 | oxidoreductase, Gfo/Idh/MocA family | | Unknown function |
| SP1691 | conserved hypothetical protein | | Hypothetical proteins-Conserved |
| SP1701 | phospho-2-dehydro-3-deoxyheptonate aldolase | | Amino acid biosynthesis |
| SP1704 | ABC transporter, ATP-binding protein | | Transport and binding proteins |
| SP1705 | hypothetical protein | | Hypothetical proteins |
| SP1738 | guanylate kinase | gmk | Purines, pyrimidines, etc |
| SP1740 | conserved hypothetical protein | | Hypothetical proteins-Conserved |
| SP1741 | conserved hypothetical protein | | Hypothetical proteins-Conserved |

TABLE 1C-continued

Conditionally essential *Streptococcus pneumoniae* genes
identified in nasopharyngeal lavage in the pneumonia model, which encode a
predicted cytoplasm-localised protein.

| SP nr. | Annotation | Gene | Mainrole |
| --- | --- | --- | --- |
| SP1743 | conserved hypothetical protein | | Hypothetical proteins-Conserved |
| SP1750 | conserved hypothetical protein | | Hypothetical proteins-Conserved |
| SP1757 | conserved hypothetical protein | | Hypothetical proteins-Conserved |
| SP1762 | hypothetical protein | | Hypothetical proteins |
| SP1799 | sugar-binding transcriptional regulator, LacI family | | Regulatory functions |
| SP1801 | conserved hypothetical protein | | Hypothetical proteins-Conserved |
| SP1802 | hypothetical protein | | Hypothetical proteins |
| SP1812 | tryptophan synthase, beta subunit | trpB | Amino acid biosynthesis |
| SP1821 | sugar-binding transcriptional regulator, LacI family | | Regulatory functions |
| SP1831 | hypothetical protein | | Hypothetical proteins |
| SP1867 | NAD-dependent epimerase/dehydratase family protein | | Energy metabolism |
| SP1892 | hypothetical protein | | Hypothetical proteins |
| SP1893 | hypothetical protein | | Hypothetical proteins |
| SP1931 | hypothetical protein, fusion | | Disrupted reading frame |
| SP1987 | ABC transporter, ATP-binding protein | | Transport and binding proteins |
| SP2006 | transcriptional regulator ComX1 | comX1 | Regulatory functions |
| SP2030 | transketolase | recP | Energy metabolism |
| SP2031 | conserved hypothetical protein | | Hypothetical proteins-Conserved |
| SP2036 | PTS system, IIA component | | Transport and binding proteins |
| SP2042 | ribonuclease P protein component | rnpA | Transcription |
| SP2056 | N-acetylglucosamine-6-phosphate deacetylase | nagA | Central intermediary metabolism |
| SP2096 | peptidase, M20/M25/M40 family | | Protein fate |
| SP2135 | ribosomal protein L33 | rpmG | Protein synthesis |
| SP2186 | glycerol kinase | gplK | Energy metabolism |
| SP2187 | conserved domain protein | | Hypothetical proteins-Domain |
| SP2206 | ribosomal subunit interface protein | yfiA | Protein synthesis |
| SP2209 | conserved hypothetical protein | | Hypothetical proteins-Conserved |
| SP2233 | hypothetical protein | | Hypothetical proteins |
| SP2234 | transcriptional regulator, TetR family | | Regulatory functions |
| SP0827 | conserved hypothetical protein, authentic point mutation | | Disrupted reading frame |
| SP0949 | IS1515, transposase, authentic frameshift | | Mobile and extrachromosomal element |
| SP0952 | alanine dehydrogenase, authentic frameshift | ald | Energy metabolism |
| SP1311 | IS66 family element, Orf3, degenerate | | Mobile and extrachromosomal element |
| SP1430 | type II restriction endonuclease, putative, authentic point mutation | | DNA metabolism |
| SP1526 | ABC transporter, ATP-binding protein authentic frameshift | | Transport and binding proteins |

TABLE 2A

Conditionally essential *Streptococcus pneumoniae* genes identified in blood
in the pneumonia model that encode a predicted surface-localised protein.

| SP nr. | Annotation | Gene | Mainrole |
| --- | --- | --- | --- |
| SP0008 | hypothetical protein | | Hypothetical proteins |
| SP0010 | conserved domain protein | | Hypothetical proteins-Domain |
| SP0529 | transport protein BlpB | blpB | Transport and binding proteins |
| SP0749 | branched-chain amino acid ABC transporter, amino acid-binding protein | livJ | Transport and binding proteins |
| SP0769 | VanZF-related protein | | Unknown function |
| SP0845 | lipoprotein | | Cell envelope |
| SP0899 | conserved hypothetical protein | | Hypothetical proteins-Conserved |
| SP1232 | membrane protein | | Cell envelope |
| SP1437 | conserved domain protein | | Hypothetical proteins-Domain |
| SP1690 | ABC transporter, substrate-binding protein | | Transport and binding proteins |
| SP1728 | hypothetical protein | | Hypothetical proteins |
| SP1955 | hypothetical protein | | Hypothetical proteins |
| SP2010 | penicillin-binding protein 2A | pbp2A | Cell envelope |
| SP2051 | competence protein CglC | cglC | Cellular processes |
| SP2084 | phosphate ABC transporter, phosphate-binding protein | pstS | Transport and binding proteins |

TABLE 2A-continued

Conditionally essential *Streptococcus pneumoniae* genes identified in blood in the pneumonia model that encode a predicted surface-localised protein.

| SP nr. | Annotation | Gene | Mainrole |
|---|---|---|---|
| SP2147 | hypothetical protein | | Hypothetical proteins |
| SP2185 | hypothetical protein | | Hypothetical proteins |
| SP2197 | ABC transporter, substrate-binding protein, putative | | Transport and binding proteins |

TABLE 2B

Conditionally essential *Streptococcus pneumoniae* genes identified in blood in the pneumonia model that encode a predicted surface-localised protein.

| SP nr. | Annotation | Gene | Mainrole |
|---|---|---|---|
| SP0062 | PTS system, IIC component | | Transport and binding proteins |
| SP0282 | PTS system, mannose-specific IID component | | Transport and binding proteins |
| SP0283 | PTS system, mannose-specific IIC component | manM | Transport and binding proteins |
| SP0324 | PTS system, IIC component | | Transport and binding proteins |
| SP0325 | PTS system, IID component | | Transport and binding proteins |
| SP0514 | hypothetical protein | | Hypothetical proteins |
| SP1185 | PTS system, lactose-specific IIBC components | lacE | Transport and binding proteins |
| SP1368 | psr protein | | Unknown function |
| SP1684 | PTS system, IIBC components | | Transport and binding proteins |
| SP2093 | hypothetical protein | | Hypothetical proteins |
| SP2205 | DHH subfamily 1 protein | | Unknown function |

TABLE 2C

Conditionally essential *Streptococcus pneumoniae* genes identified in blood in the pneumonia model that encode a predicted cytoplasm-localised protein.

| SP nr. | Annotation | Gene | Mainrole |
|---|---|---|---|
| SP0007 | S4 domain protein | | Unknown function |
| SP0029 | hypothetical protein | | Hypothetical proteins |
| SP0058 | transcriptional regulator, GntR family | | Regulatory functions |
| SP0067 | hypothetical protein | | Hypothetical proteins |
| SP0091 | ABC transporter, permease protein | | Transport and binding proteins |
| SP0097 | conserved domain protein | | Hypothetical proteins-Domain |
| SP0099 | hypothetical protein | | Hypothetical proteins |
| SP0104 | hydrolase, haloacid dehalogenase-like family | | Unknown function |
| SP0108 | hypothetical protein | | Hypothetical proteins |
| SP0111 | amino acid ABC transporter, ATP-binding protein, putative | | Transport and binding proteins |
| SP0113 | argininosuccinate synthase, truncation | argG | Disrupted reading frame |
| SP0116 | hypothetical protein | | Hypothetical proteins |
| SP0119 | MutT/nudix family protein | | DNA metabolism |
| SP0133 | hypothetical protein | | Hypothetical proteins |
| SP0135 | glycosyl transferase, putative | | Cell envelope |
| SP0138 | hypothetical protein | | Hypothetical proteins |
| SP0139 | conserved domain protein | | Hypothetical proteins-Domain |
| SP0179 | Holliday junction DNA helicase RuvA | ruvA | DNA metabolism |
| SP0180 | DNA-3-methyladenine glycosylase I | tag | DNA metabolism |
| SP0206 | hypothetical protein | | Hypothetical proteins |
| SP0245 | pyruvate formate-lyase-activating enzyme, putative | | Energy metabolism |
| SP0280 | ribosomal small subunit pseudouridine synthase A | rsuA-1 | Protein synthesis |
| SP0286 | Cof family protein | | Unknown function |
| SP0287 | xanthine/uracil permease family protein | | Transport and binding proteins |
| SP0302 | conserved domain protein | | Hypothetical proteins-Domain |
| SP0340 | autoinducer-2 production protein | luxS | Cellular processes |
| SP0400 | trigger factor | tig | Protein fate |
| SP0470 | hypothetical protein | | Hypothetical proteins |
| SP0475 | hypothetical protein | | Hypothetical proteins |
| SP0488 | conserved hypothetical protein | | Hypothetical proteins-Conserved |
| SP0489 | PAP2 family protein | | Unknown function |
| SP0507 | type I restriction-modification system, S subunit, putative | | DNA metabolism |
| SP0521 | HIT family protein | | Unknown function |
| SP0525 | blpS protein | blpS | Unknown function |
| SP0540 | blpN protein | blpN | Unknown function |
| SP0545 | immunity protein BlpY | blpY | Cellular processes |
| SP0550 | conserved hypothetical protein | | Hypothetical proteins-Conserved |
| SP0582 | hypothetical protein | | Hypothetical proteins |

TABLE 2C-continued

Conditionally essential *Streptococcus pneumoniae* genes identified in blood in the pneumonia model that encode a predicted cytoplasm-localised protein.

| SP nr. | Annotation | Gene | Mainrole |
|---|---|---|---|
| SP0603 | DNA-binding response regulator VncR | vncR/rr10 | Signal transduction |
| SP0628 | HIT family protein | | Unknown function |
| SP0635 | hypothetical protein | | Hypothetical proteins |
| SP0678 | conserved hypothetical protein | | Hypothetical proteins-Conserved |
| SP0679 | hypothetical protein | | Hypothetical proteins |
| SP0687 | ABC transporter, ATP-binding protein | | Transport and binding proteins |
| SP0696 | hypothetical protein | | Hypothetical proteins |
| SP0698 | hypothetical protein | | Hypothetical proteins |
| SP0722 | transcriptional activator TenA | tenA | Regulatory functions |
| SP0723 | conserved domain protein | thiW | Hypothetical proteins-Domain |
| SP0777 | hypothetical protein | | Hypothetical proteins |
| SP0791 | oxidoreductase, aldo/keto reductase family | | Unknown function |
| SP0792 | hypothetical protein | | Hypothetical proteins |
| SP0793 | oxidoreductase, short chain dehydrogenase/reductase family | | Unknown function |
| SP0816 | hypothetical protein | | Hypothetical proteins |
| SP0830 | hypothetical protein | | Hypothetical proteins |
| SP0831 | purine nucleoside phosphorylase, family 2 | deoD | Purines, pyrimidines, etc |
| SP0843 | deoxyribose-phosphate aldolase | deoC | Energy metabolism |
| SP0881 | thiazole biosynthesis protein ThiI | thiI | Biosynthesis of cofactors, etc |
| SP0890 | integrase/recombinase, phage integrase family | | DNA metabolism |
| SP0893 | transcriptional repressor, putative | | Regulatory functions |
| SP0901 | hypothetical protein | | Hypothetical proteins |
| SP0925 | conserved hypothetical protein | | Hypothetical proteins-Conserved |
| SP0942 | IS1381, transposase OrfA | | Mobile and extrachromosomal element |
| SP0953 | acetyltransferase, GNAT family | | Unknown function |
| SP0954 | competence protein CelA | celA | Cellular processes |
| SP0955 | competence protein CelB | celB | Cellular processes |
| SP0958 | hypothetical protein | | Hypothetical proteins |
| SP0971 | kinase, putative | | Unknown function |
| SP1009 | ferrochelatase | hemH | Biosynthesis of cofactors, etc |
| SP1011 | GtrA family protein | | Unknown function |
| SP1025 | hypothetical protein | | Hypothetical proteins |
| SP1030 | conserved hypothetical protein | | Hypothetical proteins-Conserved |
| SP1037 | type II restriction endonuclease, putative | | DNA metabolism |
| SP1038 | hypothetical protein | | Hypothetical proteins |
| SP1039 | hypothetical protein | | Hypothetical proteins |
| SP1050 | transcriptional regulator, putative | | Regulatory functions |
| SP1052 | phosphoesterase, putative | | Unknown function |
| SP1053 | conserved domain protein | | Hypothetical proteins-Domain |
| SP1054 | Tn5252, Orf 10 protein | | Mobile and extrachromosomal element |
| SP1055 | Tn5252, Orf 9 protein | | Mobile and extrachromosomal element |
| SP1061 | protein kinase, putative | | Regulatory functions |
| SP1072 | DNA primase | dnaG | DNA metabolism |
| SP1123 | glycogen biosynthesis protein GlgD | glgD | Energy metabolism |
| SP1129 | integrase/recombinase, phage integrase family | | DNA metabolism |
| SP1130 | transcriptional regulator | | Regulatory functions |
| SP1131 | transcriptional regulator, putative | | Regulatory functions |
| SP1137 | GTP-binding protein, putative | | Unknown function |
| SP1138 | hypothetical protein | | Hypothetical proteins |
| SP1139 | hypothetical protein | | Hypothetical proteins |
| SP1149 | IS630-Spn1, transposase Orf1 | | Mobile and extrachromosomal element |
| SP1166 | MATE efflux family protein | | Transport and binding proteins |
| SP1173 | conserved hypothetical protein | | Hypothetical proteins-Conserved |
| SP1177 | phosphocarrier protein HPr | ptsH | Transport and binding proteins |
| SP1178 | NrdH-redoxin | nrdH | Purines, pyrimidines, etc |
| SP1186 | PTS system, lactose-specific IIA component | lacF | Transport and binding proteins |
| SP1191 | tagatose-6-phosphate kinase | lacC | Energy metabolism |
| SP1192 | galactose-6-phosphate isomerase, LacB subunit | lacB | Energy metabolism |
| SP1209 | hypothetical protein | | Hypothetical proteins |
| SP1210 | hypothetical protein | | Hypothetical proteins |
| SP1215 | transporter, FNT family, putative | | Transport and binding proteins |
| SP1233 | hypothetical protein | | Hypothetical proteins |
| SP1245 | Cof family protein | | Unknown function |
| SP1248 | ribonuclease III | rnc | Transcription |
| SP1249 | conserved hypothetical protein | | Purines, pyrimidines, etc |
| SP1275 | carbamoyl-phosphate synthase, large subunit | carB | Purines, pyrimidines, etc |
| SP1282 | ABC transporter, ATP-binding protein | | Transport and binding proteins |

TABLE 2C-continued

Conditionally essential *Streptococcus pneumoniae* genes identified in blood in the pneumonia model that encode a predicted cytoplasm-localised protein.

| SP nr. | Annotation | Gene | Mainrole |
|---|---|---|---|
| SP1299 | ribosomal protein L31 | rpmE | Protein synthesis |
| SP1308 | toxin secretion ATP-binding protein, truncation | | Transport and binding proteins |
| SP1314 | IS66 family element, Orf1 | | Mobile and extrachromosomal element |
| SP1320 | v-type sodium ATP synthase, subunit E | ntpE | Transport and binding proteins |
| SP1322 | v-type sodium ATP synthase, subunit I | ntpI | Transport and binding proteins |
| SP1323 | hypothetical protein | | Hypothetical proteins |
| SP1331 | phosphosugar-binding transcriptional regulator, putative | | Regulatory functions |
| SP1332 | conserved domain protein | | Hypothetical proteins-Domain |
| SP1333 | hypothetical protein | | Hypothetical proteins |
| SP1339 | hypothetical protein | | Hypothetical proteins |
| SP1345 | hypothetical protein | | Hypothetical proteins |
| SP1349 | hypothetical protein | | Hypothetical proteins |
| SP1370 | shikimate kinase | aroK | Amino acid biosynthesis |
| SP1384 | conserved hypothetical protein | | Hypothetical proteins-Conserved |
| SP1393 | conserved hypothetical protein | | Hypothetical proteins-Conserved |
| SP1397 | phosphate ABC transporter, ATP-binding protein, putative | | Transport and binding proteins |
| SP1406 | hypothetical protein | | Hypothetical proteins |
| SP1422 | hypothetical protein | | Hypothetical proteins |
| SP1423 | transcriptional repressor, putative | | Regulatory functions |
| SP1426 | ABC transporter, ATP-binding protein | | Transport and binding proteins |
| SP1429 | peptidase, U32 family | | Protein fate |
| SP1442 | IS66 family element, Orf2 | | Mobile and extrachromosomal element |
| SP1450 | platelet activating factor, putative | | Fatty acid and phospholipid metab |
| SP1465 | hypothetical protein | | Hypothetical proteins |
| SP1467 | conserved hypothetical protein | | Hypothetical proteins-Conserved |
| SP1478 | oxidoreductase, aldo/keto reductase family | | Unknown function |
| SP1495 | hypothetical protein | | Hypothetical proteins |
| SP1502 | amino acid ABC transporter, permease protein | | Transport and binding proteins |
| SP1512 | ATP synthase F0, B subunit | atpF | Energy metabolism |
| SP1537 | general stress protein 13, putative | | Cellular processes |
| SP1547 | conserved hypothetical protein | | Hypothetical proteins-Conserved |
| SP1552 | cation efflux family protein | | Transport and binding proteins |
| SP1563 | pyridine nucleotide-disulphide oxidoreductase family protein | | Unknown function |
| SP1599 | tRNA pseudouridine synthase A | truA | Protein synthesis |
| SP1600 | hypothetical protein | | Cell envelope |
| SP1602 | phnA protein | phnA | Transport and binding proteins |
| SP1616 | ribulose-phosphate 3-epimerase family protein | | Energy metabolism |
| SP1619 | PTS system, IIA component | | Transport and binding proteins |
| SP1620 | PTS system, nitrogen regulatory component IIA, putative | | Transport and binding proteins |
| SP1630 | hypothetical protein | | Hypothetical proteins |
| SP1631 | threonyl-tRNA synthetase | thrS | Protein synthesis |
| SP1639 | IS1167, transposase | | Mobile and extrachromosomal element |
| SP1642 | hypothetical protein | | Hypothetical proteins |
| SP1643 | hypothetical protein | | Hypothetical proteins |
| SP1647 | endopeptidase O | pepO | Protein fate |
| SP1695 | acetyl xylan esterase, putative | | Energy metabolism |
| SP1718 | hypothetical protein | | Hypothetical proteins |
| SP1759 | preprotein translocase, SecA subunit | secA | Protein fate |
| SP1781 | conserved hypothetical protein | | Hypothetical proteins-Conserved |
| SP1787 | hypothetical protein | | Hypothetical proteins |
| SP1789 | hypothetical protein | | Hypothetical proteins |
| SP1794 | hypothetical protein | | Hypothetical proteins |
| SP1799 | sugar-binding transcriptional regulator, LacI family | | Regulatory functions |
| SP1801 | conserved hypothetical protein | | Hypothetical proteins-Conserved |
| SP1808 | type IV prepilin peptidase, putative | | Protein fate |
| SP1810 | hypothetical protein | | Hypothetical proteins |
| SP1811 | tryptophan synthase, alpha subunit | trpA | Amino acid biosynthesis |
| SP1822 | conserved domain protein | | Hypothetical proteins-Domain |
| SP1823 | MgtC/SapB family protein | | Transport and binding proteins |
| SP1824 | ABC transporter, permease protein | | Transport and binding proteins |
| SP1825 | ABC transporter, ATP-binding protein | | Transport and binding proteins |
| SP1849 | DpnD protein | dpnD | Unknown function |
| SP1851 | conserved hypothetical protein | | Hypothetical proteins-Conserved |
| SP1863 | transcriptional regulator, MarR family | | Regulatory functions |

TABLE 2C-continued

Conditionally essential *Streptococcus pneumoniae* genes identified in blood in the pneumonia model that encode a predicted cytoplasm-localised protein.

| SP nr. | Annotation | Gene | Mainrole |
|---|---|---|---|
| SP1864 | conserved hypothetical protein | | Hypothetical proteins-Conserved |
| SP1894 | sucrose phosphorylase | gftA | Energy metabolism |
| SP1899 | msm operon regulatory protein | msmR | Regulatory functions |
| SP1903 | conserved hypothetical protein | | Hypothetical proteins-Conserved |
| SP1931 | hypothetical protein, fusion | | Disrupted reading frame |
| SP1950 | bacteriocin formation protein, putative | | Cellular processes |
| SP1963 | CBS domain protein | | Unknown function |
| SP1979 | pur operon repressor | purR | Regulatory functions |
| SP1987 | ABC transporter, ATP-binding protein | | Transport and binding proteins |
| SP1988 | immunity protein, putative | | Cellular processes |
| SP1989 | transcriptional regulator PlcR, putative | | Regulatory functions |
| SP2016 | nicotinate-nucleotide pyrophosphorylase | nadC | Biosynthesis of cofactors, etc |
| SP2021 | glycosyl hydrolase, family 1 | | Energy metabolism |
| SP2023 | PTS system, IIB component | | Transport and binding proteins |
| SP2031 | conserved hypothetical protein | | Hypothetical proteins-Conserved |
| SP2054 | conserved hypothetical protein | | Hypothetical proteins-Conserved |
| SP2064 | hydrolase, haloacid dehalogenase-like family | | Unknown function |
| SP2087 | phosphate ABC transporter, ATP-binding protein | pstB | Transport and binding proteins |
| SP2088 | phosphate transport system regulatory protein PhoU | phoU | Regulatory functions |
| SP2089 | transposase, IS1380-Spn1 related, truncation | | Mobile and extrachromosomal element |
| SP2090 | transcriptional regulator | | Regulatory functions |
| SP2096 | peptidase, M20/M25/M40 family | | Protein fate |
| SP2111 | malA protein | | Energy metabolism |
| SP2115 | hypothetical protein | | Hypothetical proteins |
| SP2122 | conserved hypothetical protein | | Hypothetical proteins-Conserved |
| SP2135 | ribosomal protein L33 | rpmG | Protein synthesis |
| SP2139 | hypothetical protein | | Hypothetical proteins |
| SP2148 | arginine deiminase | arcA | Energy metabolism |
| SP2150 | ornithine carbamoyltransferase | argF | Energy metabolism |
| SP2151 | carbamate kinase | arcC | Energy metabolism |
| SP2157 | alcohol dehydrogenase, iron-containing | | Energy metabolism |
| SP2168 | fucose operon repressor, putative | | Regulatory functions |
| SP2206 | ribosomal subunit interface protein | yfiA | Protein synthesis |
| SP2229 | tryptophanyl-tRNA synthetase | trps | Protein synthesis |
| SP2233 | hypothetical protein | | Hypothetical proteins |
| SP2238 | conserved hypothetical protein | | Hypothetical proteins-Conserved |
| SP0949 | IS1515, transposase, authentic frameshift | | Mobile and extrachromosomal element |
| SP2046 | conserved domain protein, authentic frameshift | | Disrupted reading frame |
| SP2123 | transcriptional regulator, authentic frameshift | | Regulatory functions |
| SP2232 | conserved hypothetical protein, authentic frameshift | | Disrupted reading frame |

TABLE 3A

Conditionally essential *Streptococcus pneumoniae* genes identified in nasopharyngeal lavage in the colonization model, which encode a predicted surface-localised protein.

| SP nr. | Annotation | Gene | Mainrole | # Time-points identified |
|---|---|---|---|---|
| SP0042 | competence factor transporting ATP-binding/permease protein | comA | Cellular processes | 3 |
| SP0112 | amino acid ABC transporter, periplasmic amino acid-binding protein | | Transport and binding proteins | 1 |
| SP0651 | conserved hypothetical protein | | Hypothetical proteins-Conserved | 2 |
| SP1624 | acyltransferase family protein | | Unknown function | 3 |
| SP1690 | ABC transporter, substrate-binding protein | | Transport and binding proteins | 2 |
| SP1728 | hypothetical protein | | Hypothetical proteins | 2 |
| SP1955 | hypothetical protein | | Hypothetical proteins | 2 |
| SP2084 | phosphate ABC transporter, phosphate-binding protein | pstS | Transport and binding proteins | 2 |
| SP0034 | membrane protein | | Cell envelope | 1 |

TABLE 3A-continued

Conditionally essential *Streptococcus pneumoniae* genes identified in nasopharyngeal lavage in the colonization model, which encode a predicted surface-localised protein.

| SP nr. | Annotation | Gene | Mainrole | # Time-points identified |
|---|---|---|---|---|
| SP0079 | potassium uptake protein, Trk family | | Transport and binding proteins | 2 |
| SP0149 | lipoprotein | | Cell envelope | 1 |
| SP0528 | peptide pheromone BlpC | blpC | Cellular processes | 2 |
| SP1069 | conserved hypothetical protein | | Hypothetical proteins-Conserved | 3 |
| SP1379 | hypothetical protein | | Hypothetical proteins | 2 |
| SP1394 | amino acid ABC transporter, amino acid-binding protein | | Transport and binding proteins | 2 |
| SP1873 | conserved hypothetical protein | | Hypothetical proteins-Conserved | 2 |
| SP1947 | hypothetical protein | | Hypothetical proteins | 1 |
| SP1954 | serine protease, subtilase family, authentic frameshift | | Protein fate | 1 |
| SP2063 | LysM domain protein, authentic frameshift | | Cell envelope | 1 |

TABLE 3B

Conditionally essential *Streptococcus pneumoniae* genes identified in nasopharyngeal lavage in the colonization model, which encode a predicted surface-localised protein.

| SP nr. | Annotation | Gene | Mainrole | # Time-points identified |
|---|---|---|---|---|
| SP0283 | PTS system, mannose-specific IIC component | manM | Transport and binding proteins | 3 |
| SP0514 | hypothetical protein | | Hypothetical proteins | 2 |
| SP0866 | hypothetical protein | | Hypothetical proteins | 3 |
| SP0910 | conserved hypothetical protein | | Hypothetical proteins-Conserved | 1 |
| SP2161 | PTS system, IID component | | Transport and binding proteins | 2 |
| SP2205 | DHH subfamily 1 protein | | Unknown function | 4 |

TABLE 3C

Conditionally essential *Streptococcus pneumoniae* genes identified in nasopharyngeal lavage in the colonization model, which encode a predicted cytoplasm-localised protein.

| SP nr. | Annotation | Gene | Mainrole | # Time-points identified |
|---|---|---|---|---|
| SP0029 | hypothetical protein | | Hypothetical proteins | 3 |
| SP0058 | transcriptional regulator, GntR family | | Regulatory functions | 3 |
| SP0067 | hypothetical protein | | Hypothetical proteins | 1 |
| SP0104 | hydrolase, haloacid dehalogenase-like family | | Unknown function | 2 |
| SP0106 | L-serine dehydratase, iron-sulfur-dependent, beta subunit | sdhB | Energy metabolism | 1 |
| SP0111 | amino acid ABC transporter, ATP-binding protein, putative | | Transport and binding proteins | 2 |
| SP0113 | argininosuccinate synthase, truncation | argG | Disrupted reading frame | 2 |
| SP0116 | hypothetical protein | | Hypothetical proteins | 1 |
| SP0133 | hypothetical protein | | Hypothetical proteins | 2 |
| SP0152 | ABC transporter, permease protein, putative | | Transport and binding proteins | 3 |
| SP0179 | Holliday junction DNA helicase RuvA | ruvA | DNA metabolism | 2 |
| SP0200 | competence-induced protein Ccs4 | ccs4 | Unknown function | 1 |
| SP0206 | hypothetical protein | | Hypothetical proteins | 2 |
| SP0245 | pyruvate formate-lyase-activating enzyme, putative | | Energy metabolism | 2 |
| SP0302 | conserved domain protein | | Hypothetical proteins-Domain | 2 |
| SP0470 | hypothetical protein | | Hypothetical proteins | 2 |
| SP0473 | ROK family protein | | Regulatory functions | 3 |
| SP0475 | hypothetical protein | | Hypothetical proteins | 1 |
| SP0507 | type I restriction-modification system, S subunit, putative | | DNA metabolism | 2 |
| SP0521 | HIT family protein | | Unknown function | 2 |
| SP0545 | immunity protein BlpY | blpY | Cellular processes | 2 |

TABLE 3C-continued

Conditionally essential *Streptococcus pneumoniae* genes identified in nasopharyngeal lavage in the colonization model, which encode a predicted cytoplasm-localised protein.

| SP nr. | Annotation | Gene | Mainrole | # Time-points identified |
|---|---|---|---|---|
| SP0582 | hypothetical protein | | Hypothetical proteins | 1 |
| SP0585 | 5-methyltetrahydropteroyltriglutamate | metE | Amino acid biosynthesis | 3 |
| SP0635 | hypothetical protein | | Hypothetical proteins | 2 |
| SP0678 | conserved hypothetical protein | | Hypothetical proteins-Conserved | 2 |
| SP0679 | hypothetical protein | | Hypothetical proteins | 2 |
| SP0695 | HesA/MoeB/ThiF family protein | | Unknown function | 3 |
| SP0696 | hypothetical protein | | Hypothetical proteins | 2 |
| SP0698 | hypothetical protein | | Hypothetical proteins | 2 |
| SP0743 | transcriptional regulator, TetR family | | Regulatory functions | 3 |
| SP0744 | cytidine and deoxycytidylate deaminase family protein | | Unknown function | 3 |
| SP0745 | uracil phosphoribosyltransferase | upp | Purines, pyrimidines, etc | 3 |
| SP0748 | conserved hypothetical protein | | Hypothetical proteins-Conserved | 2 |
| SP0751 | branched-chain amino acid ABC transporter, permease protein | livM | Transport and binding proteins | 2 |
| SP0752 | branched-chain amino acid ABC transporter, ATP-binding protein | livG | Transport and binding proteins | 2 |
| SP0754 | acetoin utilization protein AcuB, putative | acuB | Energy metabolism | 2 |
| SP0791 | oxidoreductase, aldo/keto reductase family | | Unknown function | 1 |
| SP0792 | hypothetical protein | | Hypothetical proteins | 2 |
| SP0848 | sugar ABC transporter, permease protein, putative | | Transport and binding proteins | 2 |
| SP0881 | thiazole biosynthesis protein ThiI | thiI | Biosynthesis of cofactors, etc | 2 |
| SP0901 | hypothetical protein | | Hypothetical proteins | 2 |
| SP0949 | IS1515, transposase, authentic frameshift | | Mobile and extrachromosomal element | 3 |
| SP0953 | acetyltransferase, GNAT family | | Unknown function | 1 |
| SP0962 | lactoylglutathione lyase | gloA | Energy metabolism | 1 |
| SP1011 | GtrA family protein | | Unknown function | 4 |
| SP1025 | hypothetical protein | | Hypothetical proteins | 3 |
| SP1030 | conserved hypothetical protein | | Hypothetical proteins-Conserved | 2 |
| SP1050 | transcriptional regulator, putative | | Regulatory functions | 2 |
| SP1052 | phosphoesterase, putative | | Unknown function | 1 |
| SP1053 | conserved domain protein | | Hypothetical proteins-Domain | 2 |
| SP1054 | Tn5252, Orf 1 protein | | Mobile and extrachromosomal element | 1 |
| SP1055 | Tn5252, Orf 9 protein | | Mobile and extrachromosomal element | 2 |
| SP1061 | protein kinase, putative | | Regulatory functions | 3 |
| SP1096 | conserved hypothetical protein | | Hypothetical proteins-Conserved | 3 |
| SP1129 | integrase/recombinase, phage integrase family | | DNA metabolism | 1 |
| SP1131 | transcriptional regulator, putative | | Regulatory functions | 2 |
| SP1138 | hypothetical protein | | Hypothetical proteins | 4 |
| SP1166 | MATE efflux family protein | | Transport and binding proteins | 2 |
| SP1173 | conserved hypothetical protein | | Hypothetical proteins-Conserved | 1 |
| SP1178 | NrdH-redoxin | nrdH | Purines, pyrimidines, etc | 3 |
| SP1186 | PTS system, lactose-specific IIA component | lacF | Transport and binding proteins | 2 |
| SP1209 | hypothetical protein | | Hypothetical proteins | 2 |
| SP1210 | hypothetical protein | | Hypothetical proteins | 2 |
| SP1233 | hypothetical protein | | Hypothetical proteins | 1 |
| SP1245 | Cof family protein | | Unknown function | 2 |
| SP1289 | hypothetical protein | | Hypothetical proteins | 2 |
| SP1298 | DHH subfamily 1 protein | | Unknown function | 3 |
| SP1299 | ribosomal protein L31 | rpmE | Protein synthesis | 4 |
| SP1322 | v-type sodium ATP synthase, subunit I | ntpI | Transport and binding proteins | 2 |
| SP1323 | hypothetical protein | | Hypothetical proteins | 3 |
| SP1341 | ABC transporter, ATP-binding protein | | Transport and binding proteins | 1 |
| SP1376 | shikimate 5-dehydrogenase | aroE | Amino acid biosynthesis | 2 |
| SP1393 | conserved hypothetical protein | | Hypothetical proteins-Conserved | 3 |
| SP1397 | phosphate ABC transporter, ATP-binding protein, putative | | Transport and binding proteins | 4 |
| SP1422 | hypothetical protein | | Hypothetical proteins | 2 |

TABLE 3C-continued

Conditionally essential *Streptococcus pneumoniae* genes identified in nasopharyngeal lavage in the colonization model, which encode a predicted cytoplasm-localised protein.

| SP nr. | Annotation | Gene | Mainrole | # Time-points identified |
|---|---|---|---|---|
| SP1430 | type II restriction endonuclease, putative, authentic point mutation | | DNA metabolism | 3 |
| SP1465 | hypothetical protein | | Hypothetical proteins | 3 |
| SP1467 | conserved hypothetical protein | | Hypothetical proteins-Conserved | 2 |
| SP1495 | hypothetical protein | | Hypothetical proteins | 1 |
| SP1502 | amino acid ABC transporter, permease protein | | Transport and binding proteins | 2 |
| SP1537 | general stress protein 13, putative | | Cellular processes | 3 |
| SP1552 | cation efflux family protein | | Transport and binding proteins | 1 |
| SP1563 | pyridine nucleotide-disulphide oxidoreductase family protein | | Unknown function | 3 |
| SP1567 | endoribonuclease L-PSP | | Transcription | 2 |
| SP1568 | GTP-binding protein | | Unknown function | 2 |
| SP1599 | tRNA pseudouridine synthase A | truA | Protein synthesis | 2 |
| SP1609 | conserved hypothetical protein | | Hypothetical proteins-Conserved | 2 |
| SP1616 | ribulose-phosphate 3-epimerase family protein | | Energy metabolism | 2 |
| SP1620 | PTS system, nitrogen regulatory component IIA, putative | | Transport and binding proteins | 3 |
| SP1626 | ribosomal protein S15 | rpsO | Protein synthesis | 2 |
| SP1639 | IS1167, transposase | | Mobile and extrachromosomal element | 1 |
| SP1691 | conserved hypothetical protein | | Hypothetical proteins-Conserved | 2 |
| SP1704 | ABC transporter, ATP-binding protein | | Transport and binding proteins | 1 |
| SP1705 | hypothetical protein | | Hypothetical proteins | 1 |
| SP1718 | hypothetical protein | | Hypothetical proteins | 2 |
| SP1759 | preprotein translocase, SecA subunit | secA | Protein fate | 1 |
| SP1787 | hypothetical protein | | Hypothetical proteins | 1 |
| SP1794 | hypothetical protein | | Hypothetical proteins | 3 |
| SP1801 | conserved hypothetical protein | | Hypothetical proteins-Conserved | 2 |
| SP1802 | hypothetical protein | | Hypothetical proteins | 2 |
| SP1810 | hypothetical protein | | Hypothetical proteins | 2 |
| SP1811 | tryptophan synthase, alpha subunit | trpA | Amino acid biosynthesis | 3 |
| SP1821 | sugar-binding transcriptional regulator, LacI family | | Regulatory functions | 3 |
| SP1822 | conserved domain protein | | Hypothetical proteins-Domain | 2 |
| SP1823 | MgtC/SapB family protein | | Transport and binding proteins | 2 |
| SP1824 | ABC transporter, permease protein | | Transport and binding proteins | 1 |
| SP1825 | ABC transporter, ATP-binding protein | | Transport and binding proteins | 1 |
| SP1831 | hypothetical protein | | Hypothetical proteins | 2 |
| SP1851 | conserved hypothetical protein | | Hypothetical proteins-Conserved | 3 |
| SP1863 | transcriptional regulator, MarR family | | Regulatory functions | 1 |
| SP1864 | conserved hypothetical protein | | Hypothetical proteins-Conserved | 1 |
| SP1899 | msm operon regulatory protein | msmR | Regulatory functions | 2 |
| SP1931 | hypothetical protein, fusion | | Disrupted reading frame | 3 |
| SP1963 | CBS domain protein | | Unknown function | 2 |
| SP1979 | pur operon repressor | purR | Regulatory functions | 3 |
| SP1989 | transcriptional regulator PlcR, putative | | Regulatory functions | 2 |
| SP2006 | transcriptional regulator ComX1 | comX1 | Regulatory functions | 3 |
| SP2021 | glycosyl hydrolase, family 1 | | Energy metabolism | 2 |
| SP2031 | conserved hypothetical protein | | Hypothetical proteins-Conserved | 3 |
| SP2036 | PTS system, IIA component | | Transport and binding proteins | 3 |
| SP2042 | ribonuclease P protein component | rnpA | Transcription | 2 |
| SP2054 | conserved hypothetical protein | | Hypothetical proteins-Conserved | 2 |
| SP2056 | N-acetylglucosamine-6-phosphate deacetylase | nagA | Central intermediary metabolism | 2 |
| SP2064 | hydrolase, haloacid dehalogenase-like family | | Unknown function | 2 |
| SP2088 | phosphate transport system regulatory protein PhoU | phoU | Regulatory functions | 2 |
| SP2089 | transposase, IS138-Spn1 related, truncation | | Mobile and extrachromosomal element | 2 |

TABLE 3C-continued

Conditionally essential *Streptococcus pneumoniae* genes identified in nasopharyngeal lavage in the colonization model, which encode a predicted cytoplasm-localised protein.

| SP nr. | Annotation | Gene | Mainrole | # Time-points identified |
|---|---|---|---|---|
| SP2090 | transcriptional regulator | | Regulatory functions | 2 |
| SP2096 | peptidase, M2/M25/M4 family | | Protein fate | 2 |
| SP2115 | hypothetical protein | | Hypothetical proteins | 3 |
| SP2150 | ornithine carbamoyltransferase | argF | Energy metabolism | 2 |
| SP2151 | carbamate kinase | arcC | Energy metabolism | 1 |
| SP2206 | ribosomal subunit interface protein | yfiA | Protein synthesis | 4 |
| SP2209 | conserved hypothetical protein | | Hypothetical proteins-Conserved | 4 |
| SP2229 | tryptophanyl-tRNA synthetase | trps | Protein synthesis | 1 |
| SP2232 | conserved hypothetical protein, authentic frameshift | | Disrupted reading frame | 3 |
| SP2238 | conserved hypothetical protein | | Hypothetical proteins-Conserved | 2 |
| SP0018 | hypothetical protein | | Hypothetical proteins | 2 |
| SP0026 | hypothetical protein | | Hypothetical proteins | 2 |
| SP0046 | amidophosphoribosyltransferase | purF | Purines, pyrimidines, etc | 3 |
| SP0060 | beta-galactosidase | bga | Energy metabolism | 1 |
| SP0064 | PTS system, IIA component | | Transport and binding proteins | 1 |
| SP0072 | hypothetical protein | | Hypothetical proteins | 2 |
| SP0081 | glycosyl transferase, family 2, authentic point mutation | | Cell envelope | 2 |
| SP0096 | hypothetical protein | | Hypothetical proteins | 1 |
| SP0101 | conserved hypothetical protein | | Hypothetical proteins-Conserved | 1 |
| SP0151 | ABC transporter, ATP-binding protein | | Transport and binding proteins | 2 |
| SP0158 | NrdI family protein | | Unknown function | 1 |
| SP0166 | pyridoxal-dependent decarboxylase, Orn/Lys/Arg family | | Unknown function | 2 |
| SP0197 | dihydrofolate synthetase, putative | | Biosynthesis of cofactors, etc | 4 |
| SP0204 | acetyltransferase, GNAT family | | Unknown function | 1 |
| SP0205 | anaerobic ribonucleoside-triphosphate reductase activating protein | nrdG | Purines, pyrimidines, etc | 1 |
| SP0207 | conserved domain protein | | Hypothetical proteins-Domain | 2 |
| SP0276 | conserved hypothetical protein | | Hypothetical proteins-Conserved | 2 |
| SP0279 | conserved hypothetical protein | | Hypothetical proteins-Conserved | 2 |
| SP0303 | 6-phospho-beta-glucosidase | bglA | Energy metabolism | 2 |
| SP0304 | conserved hypothetical protein | | Hypothetical proteins-Conserved | 3 |
| SP0309 | hypothetical protein | | Hypothetical proteins | 1 |
| SP0342 | glucan 1,6-alpha-glucosidase | dexB | Cell envelope | 3 |
| SP0362 | IS66 family element, Orf3, degenerate | | Mobile and extrachromosomal element | 2 |
| SP0412 | conserved hypothetical protein | | Hypothetical proteins-Conserved | 2 |
| SP0416 | transcriptional regulator, MarR family | | Regulatory functions | 2 |
| SP0477 | 6-phospho-beta-galactosidase | lacG | Energy metabolism | 2 |
| SP0534 | hypothetical protein | | Hypothetical proteins | 1 |
| SP0546 | BlpZ protein, fusion | blpZ | Unknown function | 3 |
| SP0547 | conserved domain protein | | Hypothetical proteins-Domain | 1 |
| SP0552 | conserved hypothetical protein | | Unknown function | 4 |
| SP0559 | hypothetical protein | | Hypothetical proteins | 2 |
| SP0560 | hypothetical protein | | Hypothetical proteins | 3 |
| SP0566 | acetyltransferase, GNAT family | | Unknown function | 2 |
| SP0587 | hypothetical protein | | Hypothetical proteins | 4 |
| SP0588 | polyribonucleotide nucleotidyltransferase | pnp | Transcription | 3 |
| SP0597 | group II intron, maturase, degenerate | | Mobile and extrachromosomal element | 1 |
| SP0621 | hypothetical protein | | Hypothetical proteins | 1 |
| SP0626 | branched-chain amino acid transport system II carrier protein | brnQ | Transport and binding proteins | 2 |
| SP0646 | PTS system, IIB component, putative | | Transport and binding proteins | 1 |
| SP0706 | hypothetical protein | | Hypothetical proteins | 2 |
| SP0717 | hydroxyethylthiazole kinase | thiM | Biosynthesis of cofactors, etc | 2 |
| SP0718 | thiamine-phosphate pyrophosphorylase | thiE | Biosynthesis of cofactors, etc | 2 |
| SP0721 | conserved hypothetical protein | | Hypothetical proteins-Conserved | 2 |

TABLE 3C-continued

Conditionally essential *Streptococcus pneumoniae* genes identified in nasopharyngeal lavage in the colonization model, which encode a predicted cytoplasm-localised protein.

| SP nr. | Annotation | Gene | Mainrole | # Time-points identified |
|---|---|---|---|---|
| SP0727 | transcriptional repressor, putative | | Regulatory functions | 2 |
| SP0731 | conserved domain protein | | Hypothetical proteins-Domain | 4 |
| SP0770 | ABC transporter, ATP-binding protein | | Transport and binding proteins | 1 |
| SP0796 | conserved hypothetical protein | | Hypothetical proteins-Conserved | 2 |
| SP0810 | hypothetical protein | | Hypothetical proteins | 3 |
| SP0822 | conserved hypothetical protein | | Hypothetical proteins-Conserved | 2 |
| SP0826 | hypothetical protein | | Hypothetical proteins | 1 |
| SP0846 | sugar ABC transporter, ATP-binding protein | | Transport and binding proteins | 2 |
| SP0847 | sugar ABC transporter, permease protein, putative | | Transport and binding proteins | 2 |
| SP0861 | hypothetical protein | | Hypothetical proteins | 3 |
| SP0888 | hypothetical protein | | Hypothetical proteins | 2 |
| SP0935 | thymidylate kinase | tmk | Purines, pyrimidines, etc | 2 |
| SP0963 | dihydroorotate dehydrogenase, electron transfer subunit | pyrK | Purines, pyrimidines, etc | 1 |
| SP0980 | O-methyltransferase | | Unknown function | 3 |
| SP1010 | large conductance mechanosensitive channel protein MscL | mscL | Transport and binding proteins | 1 |
| SP1051 | conserved hypothetical protein | | Hypothetical proteins-Conserved | 2 |
| SP1059 | hypothetical protein | | Hypothetical proteins | 2 |
| SP1060 | hypothetical protein | | Hypothetical proteins | 2 |
| SP1062 | ABC transporter, ATP-binding protein | | Transport and binding proteins | 3 |
| SP1063 | ABC-2 transporter, permease protein, putative | | Transport and binding proteins | 3 |
| SP1095 | ribose-phosphate pyrophosphokinase | prsA | Purines, pyrimidines, etc | 2 |
| SP1097 | conserved hypothetical protein | | Hypothetical proteins-Conserved | 2 |
| SP1105 | ribosomal protein L21 | rplU | Protein synthesis | 1 |
| SP1109 | hypothetical protein | | Hypothetical proteins | 2 |
| SP1162 | acetoin dehydrogenase complex, E2 component | | Energy metabolism | 2 |
| SP1189 | hypothetical protein | | Hypothetical proteins | 3 |
| SP1208 | uridine kinase | udk | Purines, pyrimidines, etc | 1 |
| SP1218 | conserved hypothetical protein | | Hypothetical proteins-Conserved | 3 |
| SP1219 | DNA gyrase subunit A | gyrA | DNA metabolism | 3 |
| SP1224 | conserved domain protein | | Hypothetical proteins-Domain | 2 |
| SP1242 | amino acid ABC transporter, ATP-binding protein | | Transport and binding proteins | 3 |
| SP1259 | conserved hypothetical protein | | Hypothetical proteins-Conserved | 2 |
| SP1284 | lemA protein | lemA | Unknown function | 1 |
| SP1296 | chorismate mutase, putative | | Amino acid biosynthesis | 2 |
| SP1297 | flavodoxin | fld | Energy metabolism | 4 |
| SP1302 | conserved hypothetical protein | | Hypothetical proteins-Conserved | 1 |
| SP1325 | oxidoreductase, Gfo/Idh/MocA family | | Unknown function | 2 |
| SP1327 | conserved hypothetical protein | | Hypothetical proteins-Conserved | 2 |
| SP1340 | hypothetical protein | | Hypothetical proteins | 2 |
| SP1353 | hypothetical protein | | Hypothetical proteins | 1 |
| SP1392 | alpha-acetolactate decarboxylase | aldB | Energy metabolism | 2 |
| SP1408 | acyl-ACP thioesterase, putative | | Fatty acid and phospholipid metab | 2 |
| SP1460 | amino acid ABC transporter, ATP-binding protein | | Transport and binding proteins | 3 |
| SP1462 | conserved hypothetical protein | | Hypothetical proteins-Conserved | 1 |
| SP1466 | hemolysin | | Cellular processes | 3 |
| SP1480 | hypothetical protein | | Hypothetical proteins | 2 |
| SP1481 | hypothetical protein | | Hypothetical proteins | 2 |
| SP1494 | hypothetical protein | | Hypothetical proteins | 1 |
| SP1507 | ATP synthase F1, epsilon subunit | atpC | Energy metabolism | 4 |
| SP1615 | transketolase, authentic frameshift | recP | Energy metabolism | 1 |
| SP1618 | PTS system, IIB component | | Transport and binding proteins | 3 |
| SP1628 | hypothetical protein | | Hypothetical proteins | 1 |

TABLE 3C-continued

Conditionally essential *Streptococcus pneumoniae* genes identified in nasopharyngeal lavage in the colonization model, which encode a predicted cytoplasm-localised protein.

| SP nr. | Annotation | Gene | Mainrole | # Time-points identified |
|---|---|---|---|---|
| SP1648 | manganese ABC transporter, ATP-binding protein | psaB | Transport and binding proteins | 1 |
| SP1651 | thiol peroxidase | psaD | Cellular processes | 1 |
| SP1676 | N-acetylneuraminate lyase, putative | | Energy metabolism | 3 |
| SP1680 | conserved hypothetical protein | | Hypothetical proteins-Conserved | 1 |
| SP1681 | sugar ABC transporter, permease protein | | Transport and binding proteins | 1 |
| SP1682 | sugar ABC transporter, permease protein | | Transport and binding proteins | 2 |
| SP1708 | hypothetical protein | | Hypothetical proteins | 2 |
| SP1725 | sucrose operon repressor | scrR | Regulatory functions | 2 |
| SP1730 | hypothetical protein | | Hypothetical proteins | 2 |
| SP1734 | rRNA methyltransferase RsmB | rsmB | Protein synthesis | 2 |
| SP1751 | magnesium transporter, CorA family, putative | | Transport and binding proteins | 2 |
| SP1754 | conserved hypothetical protein | | Hypothetical proteins-Conserved | 1 |
| SP1765 | glycosyl transferase, family 8 | | Cell envelope | 1 |
| SP1767 | glycosyl transferase, family 8 | | Cell envelope | 1 |
| SP1806 | conserved domain protein | | Hypothetical proteins-Domain | 3 |
| SP1852 | galactose-1-phosphate uridylyltransferase | galT | Energy metabolism | 4 |
| SP1908 | single-strand DNA-binding protein, authentic point mutation | ssbB | DNA metabolism | 2 |
| SP1917 | hypothetical protein | | Hypothetical proteins | 2 |
| SP1920 | transcriptional regulator, MarR family | | Regulatory functions | 2 |
| SP1944 | conserved hypothetical protein TIGR15 | | Hypothetical proteins-Conserved | 1 |
| SP1946 | transcriptional regulator PlcR, putative | | Regulatory functions | 2 |
| SP1958 | hypothetical protein | | Hypothetical proteins | 2 |
| SP1974 | acylphosphatase | | Fatty acid and phospholipid metab | 2 |
| SP1995 | conserved hypothetical protein | | Hypothetical proteins-Conserved | 3 |
| SP1996 | universal stress protein family | | Cellular processes | 3 |
| SP2032 | transcriptional regulator, BglG family | | Regulatory functions | 1 |
| SP2034 | hexulose-6-phosphate isomerase, putative | | Energy metabolism | 3 |
| SP2035 | hexulose-6-phosphate synthase, putative | | Energy metabolism | 2 |
| SP2044 | acetate kinase | ackA | Energy metabolism | 3 |
| SP2062 | transcriptional regulator, MarR family | | Regulatory functions | 2 |
| SP2069 | glutamyl-tRNA synthetase | gltx | Protein synthesis | 2 |
| SP2081 | conserved hypothetical protein | | Hypothetical proteins-Conserved | 2 |
| SP2094 | conserved hypothetical protein | | Hypothetical proteins-Conserved | 3 |
| SP2102 | hypothetical protein | | Hypothetical proteins | 1 |
| SP2113 | conserved hypothetical protein | | Hypothetical proteins-Conserved | 1 |
| SP2117 | hypothetical protein | | Hypothetical proteins | 4 |
| SP2133 | conserved domain protein | | Hypothetical proteins-Domain | 2 |
| SP2180 | conserved hypothetical protein, interruption | | Disrupted reading frame | 1 |
| SP2183 | hypothetical protein | | Hypothetical proteins | 1 |
| SP2208 | helicase, putative | | Unknown function | 4 |
| SP2219 | conserved hypothetical protein | | Hypothetical proteins-Conserved | 2 |
| SP0843 | deoxyribose-phosphate | | Energy metabolism | 3 |
| SP1349 | hypothetical protein | | Hypothetical proteins | 2 |
| SP1812 | tryptophan synthase, beta | | Amino acid biosynthesis | 2 |
| SP2077 | transcriptional repressor, putative | | Regulatory functions | 2 |
| SP2120 | hypothetical protein | | Hypothetical proteins | 2 |

TABLE 4A

Conditionally essential *Streptococcus pneumoniae* genes identified in blood in the bacteraemia model, which encode a predicted surface-localised protein.

| SP nr. | Annotation | Gene | Mainrole |
| --- | --- | --- | --- |
| SP0034 | membrane protein | | Cell envelope |
| SP0042 | competence factor transporting ATP-binding/permease protein | comA | Cellular processes |
| SP0098 | hypothetical protein | | Hypothetical proteins |
| SP0112 | amino acid ABC transporter, periplasmic amino acid-binding protein | | Transport and binding proteins |
| SP0529 | transport protein BlpB | blpB | Transport and binding proteins |
| SP0637 | membrane protein | | Cell envelope |
| SP0845 | lipoprotein | | Cell envelope |
| SP0899 | conserved hypothetical protein | | Hypothetical proteins-Conserved |
| SP1232 | membrane protein | | Cell envelope |
| SP1624 | acyltransferase family protein | | Unknown function |
| SP1690 | ABC transporter, substrate-binding protein | | Transport and binding proteins |
| SP1728 | hypothetical protein | | Hypothetical proteins |
| SP2010 | penicillin-binding protein 2A | pbp2A | Cell envelope |
| SP2063 | LysM domain protein, authentic frameshift | | Cell envelope |
| SP2084 | phosphate ABC transporter, phosphate-binding protein | pstS | Transport and binding proteins |
| SP2197 | ABC transporter, substrate-binding protein, putative | | Transport and binding proteins |

TABLE 4B

Conditionally essential *Streptococcus pneumoniae* genes identified in blood in the bacteraemia model, which encode a predicted surface-localised protein.

| SP nr. | Annotation | Gene | Mainrole |
| --- | --- | --- | --- |
| SP0062 | PTS system, IIC component | | Transport and binding proteins |
| SP0282 | PTS system, mannose-specific IID component | | Transport and binding proteins |
| SP0283 | PTS system, mannose-specific IIC component | manM | Transport and binding proteins |
| SP0324 | PTS system, IIC component | | Transport and binding proteins |
| SP1368 | psr protein | | Unknown function |
| SP1617 | PTS system, IIC component | | Transport and binding proteins |
| SP1684 | PTS system, IIBC components | | Transport and binding proteins |
| SP2205 | DHH subfamily 1 protein | | Unknown function |

TABLE 4C

Conditionally essential *Streptococcus pneumoniae* genes identified in blood in the bacteraemia model, which encode a predicted cytoplasm-localised protein.

| SP nr. | Annotation | Gene | Mainrole |
| --- | --- | --- | --- |
| SP0029 | hypothetical protein | | Hypothetical proteins |
| SP0058 | transcriptional regulator, GntR family | | Regulatory functions |
| SP0067 | hypothetical protein | | Hypothetical proteins |
| SP0091 | ABC transporter, permease protein | | Transport and binding proteins |
| SP0097 | conserved domain protein | | Hypothetical proteins-Domain |
| SP0099 | hypothetical protein | | Hypothetical proteins |
| SP0104 | hydrolase, haloacid dehalogenase-like family | | Unknown function |
| SP0111 | amino acid ABC transporter, ATP-binding protein, putative | | Transport and binding proteins |
| SP0113 | argininosuccinate synthase, truncation | argG | Disrupted reading frame |
| SP0133 | hypothetical protein | | Hypothetical proteins |
| SP0179 | Holliday junction DNA helicase RuvA | ruvA | DNA metabolism |
| SP0180 | DNA-3-methyladenine glycosylase I | tag | DNA metabolism |
| SP0182 | MccC family protein | | Unknown function |
| SP0280 | ribosomal small subunit pseudouridine synthase A | rsuA-1 | Protein synthesis |
| SP0286 | Cof family protein | | Unknown function |
| SP0340 | autoinducer-2 production protein | luxS | Cellular processes |
| SP0342 | glucan 1,6-alpha-glucosidase | dexB | Cell envelope |
| SP0362 | IS66 family element, Orf3, degenerate | | Mobile and extrachromosomal element |
| SP0400 | trigger factor | tig | Protein fate |
| SP0446 | acetolactate synthase, small subunit | ilvN | Amino acid biosynthesis |
| SP0475 | hypothetical protein | | Hypothetical proteins |
| SP0489 | PAP2 family protein | | Unknown function |
| SP0521 | HIT family protein | | Unknown function |
| SP0545 | immunity protein BlpY | blpY | Cellular processes |

TABLE 4C-continued

Conditionally essential *Streptococcus pneumoniae* genes identified in blood in the bacteraemia model, which encode a predicted cytoplasm-localised protein.

| SP nr. | Annotation | Gene | Mainrole |
|---|---|---|---|
| SP0550 | conserved hypothetical protein | | Hypothetical proteins-Conserved |
| SP0582 | hypothetical protein | | Hypothetical proteins |
| SP0585 | 5-methyltetrahydropteroyltriglutamate | metE | Amino acid biosynthesis |
| SP0592 | conserved hypothetical protein | | Hypothetical proteins-Conserved |
| SP0603 | DNA-binding response regulator VncR | rr10 | Signal transduction |
| SP0628 | HIT family protein | | Unknown function |
| SP0635 | hypothetical protein | | Hypothetical proteins |
| SP0678 | conserved hypothetical protein | | Hypothetical proteins-Conserved |
| SP0679 | hypothetical protein | | Hypothetical proteins |
| SP0687 | ABC transporter, ATP-binding protein | | Transport and binding proteins |
| SP0723 | conserved domain protein | thiW | Hypothetical proteins-Domain |
| SP0768 | conserved hypothetical protein | | Hypothetical proteins-Conserved |
| SP0792 | hypothetical protein | | Hypothetical proteins |
| SP0793 | oxidoreductase, short chain dehydrogenase/reductase family | | Unknown function |
| SP0810 | hypothetical protein | | Hypothetical proteins |
| SP0816 | hypothetical protein | | Hypothetical proteins |
| SP0830 | hypothetical protein | | Hypothetical proteins |
| SP0831 | purine nucleoside phosphorylase, family 2 | deoD | Purines, pyrimidines, etc |
| SP0876 | 1-phosphofructokinase, putative | | Energy metabolism |
| SP0881 | thiazole biosynthesis protein ThiI | thiI | Biosynthesis of cofactors, etc |
| SP0893 | transcriptional repressor, putative | | Regulatory functions |
| SP0925 | conserved hypothetical protein | | Hypothetical proteins-Conserved |
| SP0942 | IS1381, transposase OrfA | | Mobile and extrachromosomal element |
| SP0949 | IS1515, transposase, authentic frameshift | | Mobile and extrachromosomal element |
| SP0953 | acetyltransferase, GNAT family | | Unknown function |
| SP0955 | competence protein CelB | celB | Cellular processes |
| SP0958 | hypothetical protein | | Hypothetical proteins |
| SP0963 | dihydroorotate dehydrogenase, electron transfer subunit | pyrK | Purines, pyrimidines, etc |
| SP1011 | GtrA family protein | | Unknown function |
| SP1025 | hypothetical protein | | Hypothetical proteins |
| SP1039 | hypothetical protein | | Hypothetical proteins |
| SP1050 | transcriptional regulator, putative | | Regulatory functions |
| SP1051 | conserved hypothetical protein | | Hypothetical proteins-Conserved |
| SP1053 | conserved domain protein | | Hypothetical proteins-Domain |
| SP1054 | Tn5252, Orf 10 protein | | Mobile and extrachromosomal element |
| SP1055 | Tn5252, Orf 9 protein | | Mobile and extrachromosomal element |
| SP1072 | DNA primase | dnaG | DNA metabolism |
| SP1129 | integrase/recombinase, phage integrase family | | DNA metabolism |
| SP1131 | transcriptional regulator, putative | | Regulatory functions |
| SP1137 | GTP-binding protein, putative | | Unknown function |
| SP1166 | MATE efflux family protein | | Transport and binding proteins |
| SP1173 | conserved hypothetical protein | | Hypothetical proteins-Conserved |
| SP1191 | tagatose-6-phosphate kinase | lacC | Energy metabolism |
| SP1192 | galactose-6-phosphate isomerase, LacB subunit | lacB | Energy metabolism |
| SP1208 | uridine kinase | udk | Purines, pyrimidines, etc |
| SP1210 | hypothetical protein | | Hypothetical proteins |
| SP1215 | transporter, FNT family, putative | | Transport and binding proteins |
| SP1233 | hypothetical protein | | Hypothetical proteins |
| SP1245 | Cof family protein | | Unknown function |
| SP1259 | conserved hypothetical protein | | Hypothetical proteins-Conserved |
| SP1275 | carbamoyl-phosphate synthase, large subunit | carB | Purines, pyrimidines, etc |
| SP1282 | ABC transporter, ATP-binding protein | | Transport and binding proteins |
| SP1299 | ribosomal protein L31 | rpmE | Protein synthesis |
| SP1308 | toxin secretion ATP-binding protein, truncation | | Transport and binding proteins |
| SP1322 | v-type sodium ATP synthase, subunit I | ntpI | Transport and binding proteins |
| SP1323 | hypothetical protein | | Hypothetical proteins |
| SP1331 | phosphosugar-binding transcriptional regulator, putative | | Regulatory functions |
| SP1333 | hypothetical protein | | Hypothetical proteins |
| SP1339 | hypothetical protein | | Hypothetical proteins |
| SP1349 | hypothetical protein | | Hypothetical proteins |
| SP1384 | conserved hypothetical protein | | Hypothetical proteins-Conserved |
| SP1393 | conserved hypothetical protein | | Hypothetical proteins-Conserved |
| SP1397 | phosphate ABC transporter, ATP-binding protein, putative | | Transport and binding proteins |
| SP1406 | hypothetical protein | | Hypothetical proteins |
| SP1422 | hypothetical protein | | Hypothetical proteins |
| SP1423 | transcriptional repressor, putative | | Regulatory functions |
| SP1429 | peptidase, U32 family | | Protein fate |
| SP1450 | platelet activating factor, putative | | Fatty acid and phospholipid metab |
| SP1467 | conserved hypothetical protein | | Hypothetical proteins-Conserved |
| SP1478 | oxidoreductase, aldo/keto reductase family | | Unknown function |
| SP1512 | ATP synthase F0, B subunit | atpF | Energy metabolism |
| SP1537 | general stress protein 13, putative | | Cellular processes |
| SP1547 | conserved hypothetical protein | | Hypothetical proteins-Conserved |
| SP1552 | cation efflux family protein | | Transport and binding proteins |

TABLE 4C-continued

Conditionally essential *Streptococcus pneumoniae* genes identified in blood in the bacteraemia model, which encode a predicted cytoplasm-localised protein.

| SP nr. | Annotation | Gene | Mainrole |
|---|---|---|---|
| SP1563 | pyridine nucleotide-disulphide oxidoreductase family protein | | Unknown function |
| SP1600 | hypothetical protein | | Cell envelope |
| SP1601 | conserved hypothetical protein | | Hypothetical proteins-Conserved |
| SP1615 | transketolase, authentic frameshift | recP | Energy metabolism |
| SP1620 | PTS system, nitrogen regulatory component IIA, putative | | Transport and binding proteins |
| SP1630 | hypothetical protein | | Hypothetical proteins |
| SP1631 | threonyl-tRNA synthetase | thrS | Protein synthesis |
| SP1647 | endopeptidase O | pepO | Protein fate |
| SP1695 | acetyl xylan esterase, putative | | Energy metabolism |
| SP1750 | conserved hypothetical protein | | Hypothetical proteins-Conserved |
| SP1781 | conserved hypothetical protein | | Hypothetical proteins-Conserved |
| SP1794 | hypothetical protein | | Hypothetical proteins |
| SP1799 | sugar-binding transcriptional regulator, LacI family | | Regulatory functions |
| SP1801 | conserved hypothetical protein | | Hypothetical proteins-Conserved |
| SP1812 | tryptophan synthase, beta subunit | trpB | Amino acid biosynthesis |
| SP1825 | ABC transporter, ATP-binding protein | | Transport and binding proteins |
| SP1851 | conserved hypothetical protein | | Hypothetical proteins-Conserved |
| SP1863 | transcriptional regulator, MarR family | | Regulatory functions |
| SP1864 | conserved hypothetical protein | | Hypothetical proteins-Conserved |
| SP1899 | msm operon regulatory protein | msmR | Regulatory functions |
| SP1903 | conserved hypothetical protein | | Hypothetical proteins-Conserved |
| SP1950 | bacteriocin formation protein, putative | | Cellular processes |
| SP1963 | CBS domain protein | | Unknown function |
| SP1988 | immunity protein, putative | | Cellular processes |
| SP1989 | transcriptional regulator PlcR, putative | | Regulatory functions |
| SP2006 | transcriptional regulator ComX1 | comX1 | Regulatory functions |
| SP2016 | nicotinate-nucleotide pyrophosphorylase | nadC | Biosynthesis of cofactors, etc |
| SP2021 | glycosyl hydrolase, family 1 | | Energy metabolism |
| SP2030 | transketolase | recP | Energy metabolism |
| SP2031 | conserved hypothetical protein | | Hypothetical proteins-Conserved |
| SP2036 | PTS system, IIA component | | Transport and binding proteins |
| SP2046 | conserved domain protein, authentic frameshift | | Disrupted reading frame |
| SP2064 | hydrolase, haloacid dehalogenase-like family | | Unknown function |
| SP2090 | transcriptional regulator | | Regulatory functions |
| SP2096 | peptidase, M20/M25/M40 family | | Protein fate |
| SP2123 | transcriptional regulator, authentic frameshift | | Regulatory functions |
| SP2135 | ribosomal protein L33 | rpmG | Protein synthesis |
| SP2148 | arginine deiminase | arcA | Energy metabolism |
| SP2150 | ornithine carbamoyltransferase | argF | Energy metabolism |
| SP2151 | carbamate kinase | arcC | Energy metabolism |
| SP2157 | alcohol dehydrogenase, iron-containing | | Energy metabolism |
| SP2187 | conserved domain protein | | Hypothetical proteins-Domain |
| SP2206 | ribosomal subunit interface protein | yfiA | Protein synthesis |
| SP2233 | hypothetical protein | | Hypothetical proteins |
| SP0073 | conserved hypothetical protein | | Hypothetical proteins-Conserved |
| SP0165 | flavoprotein | | Unknown function |
| SP0341 | hypothetical protein | | Hypothetical proteins |
| SP0452 | amino acid ABC transporter, ATP-binding protein | | Transport and binding proteins |
| SP0668 | glucokinase | gki | Energy metabolism |
| SP0764 | dihydroorotate dehydrogenase A | pyrDa | Purines, pyrimidines, etc |
| SP0931 | glutamate 5-kinase | proB | Amino acid biosynthesis |
| SP1056 | Tn5252, relaxase | | Mobile and extrachromosomal element |
| SP1126 | conserved hypothetical protein TIGR00045 | | Hypothetical proteins-Conserved |
| SP1212 | tRNA pseudouridine synthase B | truB | Protein synthesis |
| SP1213 | conserved domain protein | | Hypothetical proteins-Domain |
| SP1276 | carbamoyl-phosphate synthase, small subunit | carA | Purines, pyrimidines, etc |
| SP1435 | ABC transporter, ATP-binding protein | | Transport and binding proteins |
| SP1485 | IS3-Spn1, transposase | | Mobile and extrachromosomal element |
| SP1761 | hypothetical protein | | Hypothetical proteins |
| SP1764 | glycosyl transferase, family 2 | | Cell envelope |
| SP1792 | IS1167, transposase | | Mobile and extrachromosomal element |
| SP1928 | IS1381, transposase OrfB | | Mobile and extrachromosomal element |
| SP1966 | UDP-N-acetylglucosamine 1-carboxyvinyltransferase | murA | Cell envelope |
| SP2059 | conserved hypothetical protein | | Hypothetical proteins-Conserved |
| SP2067 | hypothetical protein | | Hypothetical proteins |
| SP2126 | dihydroxy-acid dehydratase | ilvD | Amino acid biosynthesis |
| SP2127 | transketolase, C-terminal subunit | | Energy metabolism |
| SP2156 | SPFH domain/Band 7 family | | Unknown function |
| SP2160 | conserved hypothetical protein | | Hypothetical proteins-Conserved |

TABLE 5

Genes common to Tables 1-4.

| SP nr. | 1A | 2A | 3A | 4A | 1B | 2B | 3B | 4B | 1C | 2C | 3C | 4C |
|---|---|---|---|---|---|---|---|---|---|---|---|---|
| SP0034 |  |  | X | X |  |  |  |  |  |  |  |  |
| SP0042 | X |  | X | X |  |  |  |  |  |  |  |  |
| SP0112 | X |  | X | X |  |  |  |  |  |  |  |  |
| SP0529 |  | X |  | X |  |  |  |  |  |  |  |  |
| SP0651 | X |  | X |  |  |  |  |  |  |  |  |  |
| SP0749 | X | X |  |  |  |  |  |  |  |  |  |  |
| SP0769 | X | X |  |  |  |  |  |  |  |  |  |  |
| SP0845 |  | X |  | X |  |  |  |  |  |  |  |  |
| SP0899 |  | X |  | X |  |  |  |  |  |  |  |  |
| SP1232 |  | X |  | X |  |  |  |  |  |  |  |  |
| SP1437 | X | X |  |  |  |  |  |  |  |  |  |  |
| SP1624 | X |  | X | X |  |  |  |  |  |  |  |  |
| SP1690 | X | X | X | X |  |  |  |  |  |  |  |  |
| SP1728 |  | X | X | X |  |  |  |  |  |  |  |  |
| SP1955 | X | X | X |  |  |  |  |  |  |  |  |  |
| SP2010 | X | X |  | X |  |  |  |  |  |  |  |  |
| SP2063 |  |  | X | X |  |  |  |  |  |  |  |  |
| SP2084 | X | X | X | X |  |  |  |  |  |  |  |  |
| SP2147 | X | X |  |  |  |  |  |  |  |  |  |  |
| SP2197 | X | X |  | X |  |  |  |  |  |  |  |  |
| SP0062 |  |  |  |  |  | X |  | X |  |  |  |  |
| SP0282 |  |  |  |  | X | X |  | X |  |  |  |  |
| SP0283 |  |  |  |  | X | X | X | X |  |  |  |  |
| SP0324 |  |  |  |  |  | X |  | X |  |  |  |  |
| SP0514 |  |  |  |  | X | X | X |  |  |  |  |  |
| SP0866 |  |  |  |  | X |  | X |  |  |  |  |  |
| SP1368 |  |  |  |  | X | X |  | X |  |  |  |  |
| SP1617 |  |  |  |  | X |  | X |  |  |  |  |  |
| SP1684 |  |  |  |  |  | X | X |  |  |  |  |  |
| SP2205 |  |  |  |  | X | X | X | X |  |  |  |  |
| SP0029 |  |  |  |  |  |  |  |  |  | X | X | X |
| SP0058 |  |  |  |  |  |  |  |  | X | X | X | X |
| SP0067 |  |  |  |  |  |  |  |  |  | X | X | X |
| SP0091 |  |  |  |  |  |  |  |  |  | X |  | X |
| SP0097 |  |  |  |  |  |  |  |  |  | X |  | X |
| SP0099 |  |  |  |  |  |  |  |  |  | X |  | X |
| SP0104 |  |  |  |  |  |  |  |  |  | X | X | X |
| SP0106 |  |  |  |  |  |  |  |  | X |  | X |  |
| SP0111 |  |  |  |  |  |  |  |  |  | X | X | X |
| SP0113 |  |  |  |  |  |  |  |  |  | X | X | X |
| SP0116 |  |  |  |  |  |  |  |  |  | X | X | X |
| SP0133 |  |  |  |  |  |  |  |  |  | X | X | X |
| SP0152 |  |  |  |  |  |  |  |  | X |  | X |  |
| SP0179 |  |  |  |  |  |  |  |  |  | X | X | X |
| SP0180 |  |  |  |  |  |  |  |  |  | X |  | X |
| SP0182 |  |  |  |  |  |  |  |  |  | X |  | X |
| SP0200 |  |  |  |  |  |  |  |  |  | X | X |  |
| SP0206 |  |  |  |  |  |  |  |  |  | X | X | X |
| SP0245 |  |  |  |  |  |  |  |  |  | X | X |  |
| SP0280 |  |  |  |  |  |  |  |  |  | X |  | X |
| SP0286 |  |  |  |  |  |  |  |  |  | X |  | X |
| SP0302 |  |  |  |  |  |  |  |  |  | X | X |  |
| SP0340 |  |  |  |  |  |  |  |  |  | X |  | X |
| SP0342 |  |  |  |  |  |  |  |  |  |  | X | X |
| SP0362 |  |  |  |  |  |  |  |  |  |  | X | X |
| SP0400 |  |  |  |  |  |  |  |  |  | X |  | X |
| SP0446 |  |  |  |  |  |  |  |  | X |  |  | X |
| SP0470 |  |  |  |  |  |  |  |  |  | X | X |  |
| SP0473 |  |  |  |  |  |  |  |  |  | X | X |  |
| SP0475 |  |  |  |  |  |  |  |  |  | X | X | X |
| SP0488 |  |  |  |  |  |  |  |  | X | X |  |  |
| SP0489 |  |  |  |  |  |  |  |  |  | X |  | X |
| SP0507 |  |  |  |  |  |  |  |  |  | X | X |  |
| SP0521 |  |  |  |  |  |  |  |  |  | X | X | X |
| SP0525 |  |  |  |  |  |  |  |  |  | X | X |  |
| SP0545 |  |  |  |  |  |  |  |  |  | X | X | X |
| SP0550 |  |  |  |  |  |  |  |  |  | X |  | X |
| SP0582 |  |  |  |  |  |  |  |  |  | X | X | X |
| SP0585 |  |  |  |  |  |  |  |  | X |  |  | X |
| SP0592 |  |  |  |  |  |  |  |  | X |  |  | X |
| SP0603 |  |  |  |  |  |  |  |  |  | X |  | X |
| SP0628 |  |  |  |  |  |  |  |  |  | X |  | X |
| SP0635 |  |  |  |  |  |  |  |  |  | X | X | X |
| SP0678 |  |  |  |  |  |  |  |  |  | X | X | X |
| SP0679 |  |  |  |  |  |  |  |  |  | X | X | X |
| SP0687 |  |  |  |  |  |  |  |  | X | X |  | X |
| SP0695 |  |  |  |  |  |  |  |  | X |  | X |  |
| SP0696 |  |  |  |  |  |  |  |  | X | X | X |  |
| SP0698 |  |  |  |  |  |  |  |  |  | X | X |  |
| SP0723 |  |  |  |  |  |  |  |  |  | X |  | X |
| SP0743 |  |  |  |  |  |  |  |  | X |  | X |  |
| SP0744 |  |  |  |  |  |  |  |  | X |  | X |  |
| SP0745 |  |  |  |  |  |  |  |  | X |  | X |  |
| SP0748 |  |  |  |  |  |  |  |  | X |  | X |  |
| SP0751 |  |  |  |  |  |  |  |  | X |  | X |  |
| SP0752 |  |  |  |  |  |  |  |  | X |  | X |  |
| SP0754 |  |  |  |  |  |  |  |  | X |  | X |  |
| SP0768 |  |  |  |  |  |  |  |  | X |  |  | X |
| SP0777 |  |  |  |  |  |  |  |  | X | X |  |  |
| SP0791 |  |  |  |  |  |  |  |  |  | X | X |  |
| SP0792 |  |  |  |  |  |  |  |  |  | X | X | X |
| SP0793 |  |  |  |  |  |  |  |  |  | X |  | X |
| SP0810 |  |  |  |  |  |  |  |  |  | X |  | X |
| SP0816 |  |  |  |  |  |  |  |  | X | X |  | X |
| SP0830 |  |  |  |  |  |  |  |  | X | X |  | X |
| SP0831 |  |  |  |  |  |  |  |  | X | X |  | X |
| SP0843 |  |  |  |  |  |  |  |  |  | X | X |  |
| SP0848 |  |  |  |  |  |  |  |  | X |  |  |  |
| SP0876 |  |  |  |  |  |  |  |  | X |  |  | X |
| SP0881 |  |  |  |  |  |  |  |  | X | X | X | X |
| SP0893 |  |  |  |  |  |  |  |  | X | X |  |  |
| SP0901 |  |  |  |  |  |  |  |  |  | X | X |  |
| SP0925 |  |  |  |  |  |  |  |  | X |  |  | X |
| SP0942 |  |  |  |  |  |  |  |  |  | X |  | X |
| SP0949 |  |  |  |  |  |  |  |  | X | X | X | X |
| SP0953 |  |  |  |  |  |  |  |  |  | X | X | X |
| SP0955 |  |  |  |  |  |  |  |  |  | X |  | X |
| SP0958 |  |  |  |  |  |  |  |  |  | X |  | X |
| SP0962 |  |  |  |  |  |  |  |  | X |  | X |  |
| SP0963 |  |  |  |  |  |  |  |  |  | X |  | X |
| SP1011 |  |  |  |  |  |  |  |  | X | X | X | X |
| SP1025 |  |  |  |  |  |  |  |  | X | X | X |  |
| SP1030 |  |  |  |  |  |  |  |  |  | X | X |  |
| SP1039 |  |  |  |  |  |  |  |  | X |  | X | X |
| SP1050 |  |  |  |  |  |  |  |  |  | X | X | X |
| SP1051 |  |  |  |  |  |  |  |  |  |  | X | X |
| SP1052 |  |  |  |  |  |  |  |  |  | X | X | X |
| SP1053 |  |  |  |  |  |  |  |  |  | X | X | X |
| SP1054 |  |  |  |  |  |  |  |  |  | X | X | X |
| SP1055 |  |  |  |  |  |  |  |  |  | X | X | X |
| SP1061 |  |  |  |  |  |  |  |  | X |  | X |  |
| SP1072 |  |  |  |  |  |  |  |  |  | X |  | X |
| SP1096 |  |  |  |  |  |  |  |  | X |  | X |  |
| SP1129 |  |  |  |  |  |  |  |  |  | X | X | X |
| SP1131 |  |  |  |  |  |  |  |  |  | X | X | X |
| SP1137 |  |  |  |  |  |  |  |  |  | X |  | X |
| SP1138 |  |  |  |  |  |  |  |  |  | X | X |  |
| SP1166 |  |  |  |  |  |  |  |  |  | X | X | X |
| SP1173 |  |  |  |  |  |  |  |  |  | X | X | X |
| SP1177 |  |  |  |  |  |  |  |  | X | X |  |  |
| SP1178 |  |  |  |  |  |  |  |  |  | X | X |  |
| SP1186 |  |  |  |  |  |  |  |  |  | X | X |  |
| SP1191 |  |  |  |  |  |  |  |  |  | X |  | X |
| SP1192 |  |  |  |  |  |  |  |  |  | X |  | X |
| SP1208 |  |  |  |  |  |  |  |  |  |  | X | X |
| SP1209 |  |  |  |  |  |  |  |  |  | X | X |  |
| SP1210 |  |  |  |  |  |  |  |  |  | X | X | X |
| SP1215 |  |  |  |  |  |  |  |  |  | X | X |  |
| SP1233 |  |  |  |  |  |  |  |  |  | X | X |  |
| SP1245 |  |  |  |  |  |  |  |  | X | X | X | X |
| SP1259 |  |  |  |  |  |  |  |  |  |  | X | X |
| SP1275 |  |  |  |  |  |  |  |  |  | X | X |  |
| SP1282 |  |  |  |  |  |  |  |  |  | X | X |  |
| SP1289 |  |  |  |  |  |  |  |  | X |  | X |  |
| SP1298 |  |  |  |  |  |  |  |  | X |  | X |  |
| SP1299 |  |  |  |  |  |  |  |  |  | X | X | X |
| SP1308 |  |  |  |  |  |  |  |  |  | X |  | X |
| SP1320 |  |  |  |  |  |  |  |  | X | X |  |  |

TABLE 5-continued

Genes common to Tables 1-4.

| SP nr. | 1A | 2A | 3A | 4A | 1B | 2B | 3B | 4B | 1C | 2C | 3C | 4C |
|---|---|---|---|---|---|---|---|---|---|---|---|---|
| SP1322 | | | | | | | | | | X | X | X |
| SP1323 | | | | | | | | | | X | X | X |
| SP1331 | | | | | | | | | | X | | X |
| SP1333 | | | | | | | | | X | X | | X |
| SP1339 | | | | | | | | | | X | | X |
| SP1341 | | | | | | | | | X | | X | |
| SP1349 | | | | | | | | | | X | X | X |
| SP1370 | | | | | | | | | X | X | | |
| SP1376 | | | | | | | | | X | | X | |
| SP1384 | | | | | | | | | | X | | X |
| SP1393 | | | | | | | | | | X | X | X |
| SP1397 | | | | | | | | | X | X | X | X |
| SP1406 | | | | | | | | | | X | | X |
| SP1422 | | | | | | | | | X | X | X | X |
| SP1423 | | | | | | | | | | X | | X |
| SP1429 | | | | | | | | | X | X | | X |
| SP1430 | | | | | | | | | X | | X | |
| SP1450 | | | | | | | | | | X | | X |
| SP1465 | | | | | | | | | X | X | X | |
| SP1467 | | | | | | | | | X | X | X | X |
| SP1478 | | | | | | | | | X | X | | X |
| SP1495 | | | | | | | | | | X | X | |
| SP1502 | | | | | | | | | | X | X | |
| SP1512 | | | | | | | | | | X | | X |
| SP1537 | | | | | | | | | X | X | X | X |
| SP1547 | | | | | | | | | | X | | X |
| SP1552 | | | | | | | | | | X | X | X |
| SP1563 | | | | | | | | | X | X | X | X |
| SP1567 | | | | | | | | | | X | | X |
| SP1568 | | | | | | | | | | X | | X |
| SP1599 | | | | | | | | | | X | X | |
| SP1600 | | | | | | | | | | X | | X |
| SP1601 | | | | | | | | | | X | | X |
| SP1602 | | | | | | | | | | X | X | |
| SP1609 | | | | | | | | | | X | X | |
| SP1615 | | | | | | | | | | | X | X |
| SP1616 | | | | | | | | | X | X | | |
| SP1620 | | | | | | | | | X | X | X | |
| SP1626 | | | | | | | | | X | | X | |
| SP1630 | | | | | | | | | | X | | X |
| SP1631 | | | | | | | | | | X | | X |
| SP1639 | | | | | | | | | | X | X | |
| SP1642 | | | | | | | | | X | X | | |
| SP1643 | | | | | | | | | X | X | | |
| SP1647 | | | | | | | | | | X | | X |
| SP1691 | | | | | | | | | | X | | X |
| SP1695 | | | | | | | | | X | | X | |
| SP1704 | | | | | | | | | | X | X | |
| SP1705 | | | | | | | | | | X | | X |
| SP1718 | | | | | | | | | | X | X | |
| SP1750 | | | | | | | | | X | | | X |
| SP1759 | | | | | | | | | | X | X | |
| SP1781 | | | | | | | | | | X | | X |
| SP1787 | | | | | | | | | | X | X | |
| SP1794 | | | | | | | | | | X | X | X |
| SP1799 | | | | | | | | | X | X | X | |
| SP1801 | | | | | | | | | X | X | X | |
| SP1802 | | | | | | | | | X | | X | |
| SP1810 | | | | | | | | | | X | X | |
| SP1811 | | | | | | | | | X | | X | |
| SP1812 | | | | | | | | | X | | X | X |
| SP1821 | | | | | | | | | X | | X | |
| SP1822 | | | | | | | | | | X | X | |
| SP1823 | | | | | | | | | | X | X | |
| SP1824 | | | | | | | | | | X | X | |
| SP1825 | | | | | | | | | | X | X | X |
| SP1831 | | | | | | | | | X | | X | |
| SP1851 | | | | | | | | | | X | X | X |
| SP1863 | | | | | | | | | | X | X | X |
| SP1864 | | | | | | | | | | X | X | X |
| SP1899 | | | | | | | | | | X | X | |
| SP1903 | | | | | | | | | | X | X | |
| SP1931 | | | | | | | | | X | X | X | |
| SP1950 | | | | | | | | | | X | | X |
| SP1963 | | | | | | | | | | X | X | X |
| SP1979 | | | | | | | | | | X | X | |
| SP1987 | | | | | | | | | X | X | | |
| SP1988 | | | | | | | | | | X | | X |
| SP1989 | | | | | | | | | | X | X | X |
| SP2006 | | | | | | | | | X | | X | X |
| SP2016 | | | | | | | | | | X | X | |
| SP2021 | | | | | | | | | | X | X | X |
| SP2030 | | | | | | | | | X | | | X |
| SP2031 | | | | | | | | | X | X | X | X |
| SP2036 | | | | | | | | | X | | X | X |
| SP2042 | | | | | | | | | X | X | X | |
| SP2046 | | | | | | | | | | X | | X |
| SP2054 | | | | | | | | | | X | X | |
| SP2056 | | | | | | | | | X | | X | |
| SP2064 | | | | | | | | | | X | X | X |
| SP2088 | | | | | | | | | | X | X | |
| SP2089 | | | | | | | | | | X | X | |
| SP2090 | | | | | | | | | | X | X | X |
| SP2096 | | | | | | | | | X | X | X | X |
| SP2115 | | | | | | | | | | X | X | |
| SP2123 | | | | | | | | | | X | | X |
| SP2135 | | | | | | | | | X | X | | X |
| SP2148 | | | | | | | | | | X | | X |
| SP2150 | | | | | | | | | | X | X | X |
| SP2151 | | | | | | | | | | X | X | X |
| SP2157 | | | | | | | | | | X | | X |
| SP2187 | | | | | | | | | X | | | X |
| SP2206 | | | | | | | | | | X | X | X |
| SP2209 | | | | | | | | | X | | X | |
| SP2229 | | | | | | | | | | X | X | |
| SP2232 | | | | | | | | | | X | X | |
| SP2233 | | | | | | | | | X | X | | X |
| SP2238 | | | | | | | | | | X | X | |

TABLE 6

Genes found in the GAF screens that have been identified in literature as potential vaccine candidates.

| SP nr. | Pneumonia-NPL | Pneumonia-blood | Colonization | Bacteraemia | Ref |
|---|---|---|---|---|---|
| SP0023 | | | X | | P, H |
| SP0044 | X | | X | | P |
| SP0045 | | | | X | P, H |
| SP0049 | X | X | X | | H |
| SP0050 | X | | | | H |
| SP0053 | | | X | | P |
| SP0054 | X | | | | P |
| SP0063 | | | | X | H |
| SP0083 | | X | | | 8 |
| SP0095 | | | | X | H |
| SP0100 | | X | X | | H |
| SP0117 | | | X | | H |
| SP0143 | | X | | | P |
| SP0146 | | X | | | H |
| SP0150 | | | X | | H |
| SP0156 | | | | X | 8 |
| SP0157 | | X | | X | H |
| SP0160 | | | X | | H |
| SP0176 | | X | | | 12 |
| SP0177 | X | | | | H |
| SP0178 | X | | | | 12 |
| SP0198 | X | X | X | X | H |
| SP0199 | X | X | | X | H |
| SP0246 | X | X | | | H |
| SP0247 | X | X | X | | H |
| SP0251 | | X | | X | L, H |

TABLE 6-continued

Genes found in the GAF screens that have been identified in literature as potential vaccine candidates.

| SP nr. | Pneumonia-NPL | Pneumonia-blood | Colonization | Bacteraemia | Ref |
|---|---|---|---|---|---|
| SP0253 |  | X |  |  | H |
| SP0268 |  | X |  | X | H |
| SP0284 |  |  |  | X | L |
| SP0314 |  |  | X |  | H |
| SP0320 | X |  |  |  | H |
| SP0332 | X |  |  |  | H |
| SP0350 | X |  | X |  | 11 |
| SP0351 | X |  | X |  | 11 |
| SP0358 | X |  |  |  | 11 |
| SP0390 | X |  |  |  | 5 |
| SP0396 |  | X |  |  | H |
| SP0445 |  |  |  | X | H |
| SP0454 | X |  |  |  | H |
| SP0463 |  |  | X |  | H |
| SP0464 |  |  |  | X | H |
| SP0467 | X |  |  |  | H |
| SP0474 |  | X |  | X | H |
| SP0479 |  |  |  | X | H |
| SP0494 |  |  | X | X | H |
| SP0510 |  | X |  | X | H |
| SP0527 | X | X | X | X | 8 |
| SP0530 | X | X |  | X | H |
| SP0586 | X |  |  | X | H |
| SP0600 |  | X |  |  | H |
| SP0609 | X |  |  |  | P |
| SP0614 |  |  | X |  | H |
| SP0633 | X | X | X | X | H |
| SP0663 |  | X |  |  | H |
| SP0664 |  | X |  |  | P, H |
| SP0665 | X |  |  |  | H |
| SP0686 |  | X |  |  | H |
| SP0726 |  |  | X |  | H |
| SP0728 | X |  | X |  | H |
| SP0729 | X |  | X |  | H |
| SP0730 |  | X |  | X | 3 |
| SP0737 |  |  |  | X | 15 |
| SP0742 | X |  |  |  | P |
| SP0746 | X |  | X |  | 6 |
| SP0771 |  |  | X |  | 15 |
| SP0785 |  | X |  | X | H |
| SP0789 |  | X | X |  | H |
| SP0820 | X |  | X |  | P |
| SP0823 |  |  | X |  | L |
| SP0829 | X | X | X | X | H |
| SP0886 | X |  |  |  | H |
| SP0892 |  | X |  |  | H |
| SP0933 |  |  | X |  | L |
| SP0943 | X |  |  |  | H |
| SP0948 | X |  |  |  | P |
| SP0965 | X |  | X |  | 4 |
| SP0966 |  |  | X |  | L, H |
| SP1004 | X | X |  | X | 1 |
| SP1029 | X |  |  |  | H |
| SP1033 |  | X |  | X | L |
| SP1035 |  | X |  | X | 13 |
| SP1045 |  | X |  | X | H |
| SP1068 |  |  | X |  | L |
| SP1111 |  |  | X |  | H |
| SP1112 | X |  | X |  | H |
| SP1115 | X |  |  |  | H |
| SP1121 | X |  | X |  | H |
| SP1127 | X |  | X | X | H |
| SP1193 |  | X | X | X | H |
| SP1207 |  |  |  | X | 15 |
| SP1278 |  | X |  |  | H |
| SP1326 |  |  | X | X | 2 |
| SP1328 |  |  | X | X | H |
| SP1342 | X |  |  |  | P |
| SP1343 |  | X |  |  | H |
| SP1344 | X |  |  |  | H |
| SP1389 | X |  |  |  | P |
| SP1396 | X |  | X |  | H |
| SP1398 |  | X |  |  | H |
| SP1399 |  |  |  | X | H |
| SP1431 |  |  | X | X | H |
| SP1434 | X |  |  | X | H |
| SP1469 | X |  | X |  | L |
| SP1479 | X | X |  |  | 10 |
| SP1527 | X |  | X |  | L |
| SP1544 | X |  |  | X | H |
| SP1577 |  |  | X |  | 12 |
| SP1623 | X |  |  | X | P |
| SP1645 | X |  | X |  | H |
| SP1693 |  | X |  | X | 9 |
| SP1706 |  | X |  | X | H |
| SP1715 |  |  | X |  | L, H |
| SP1717 |  | X | X | X | H |
| SP1753 | X |  | X |  | 7 |
| SP1760 |  | X |  |  | H |
| SP1770 |  |  | X |  | H |
| SP1771 | X |  |  |  | H |
| SP1782 |  | X |  | X | P |
| SP1793 |  |  | X |  | H |
| SP1796 |  | X |  | X | 14 |
| SP1800 |  | X |  | X | H |
| SP1830 | X |  | X |  | H |
| SP1847 |  | X |  | X | H |
| SP1854 |  |  | X |  | H |
| SP1856 |  |  | X |  | H |
| SP1861 |  |  | X |  | H |
| SP1870 |  |  | X |  | 13 |
| SP1923 |  |  | X |  | H |
| SP1939 | X |  |  |  | H |
| SP1964 |  |  |  | X | H |
| SP2017 |  |  | X |  | H |
| SP2028 |  | X |  | X | 12 |
| SP2039 |  |  | X |  | H |
| SP2052 |  | X |  | X | H |
| SP2082 | X |  |  |  | 8 |
| SP2083 | X |  |  |  | 8 |
| SP2091 | X |  |  | X | L |
| SP2098 | X |  | X | X | H |
| SP2116 | X | X | X | X | P |
| SP2143 |  |  |  | X | H |
| SP2145 |  | X |  | X | L, H |
| SP2163 |  | X |  |  | 7 |
| SP2164 |  | X |  |  | H |
| SP2175 |  | X |  | X | H |
| SP2176 |  | X |  |  | H |
| SP2193 |  |  | X |  | 8 |
| SP2231 | X | X | X |  | H |
| SP2236 |  | X |  |  | L, H |
| SP2240 |  |  | X |  | 12 |

Indicated literature references are: H: Hava et al., 2002, Mol. Microbiol. 45: 1389-1406; L: Lau et al., 2001, Mol. Microbiol. 40: 555-571; P: Polissi et al., 1998, Infect. Immun. 66: 5620-5629; 1: Adamou et al., 2001, Infect. Immun. 69: 949-958; 2: Berry et al., 1996, J. Bacteriol. 178: 4854-4860; 3: Spellerberg et al., 1996, Mol. Microbiol. 19: 803-813; 4: Garcia et al., 1999, Mol. Microbiol. 31: 1275-1281; 5: Gosink et al., 2000, Infect. immun. 68: 5690-5695; 6: Kwon et al., 2003, Infect. Immun. 71: 3757-3765; 7: Orihuela et al., 2004, Infect. Immun. 72: 5582-5596; 8: Throup et al., 2000, Mol. Microbiol. 35: 566-576; 9: Tong et al., 2000, Infect. Immun. 68: 921-924; 10: Vollmer et al., 2002, Infect. Immun. 70: 7176-7178; 11: Caimano, M. J. et al., in: Streptococcus pneumoniae - Molecular biology and mechanisms of disease, A. Tomasz (Ed.), Mary Ann Liebert, Larchmont, NY, 2000, p. 115. 12: Marra, A. et al., 2002, Infect. Immun. 70: 1422-1433; 13: Brown, J. S. et al., 2001, Infect. Immun. 69: 6702-6706; 14: Iyer R. and Camilli A., 2007, Mol. Microbiol. 66: 1-13; 15: Zysk G. et al., 2000, Infect Immun. 68: 3740-3743.

The proteins encoded by the genes listed in Table 1A-C, 2A-C, 3A-C, and/or 4A-C may be used to produce vaccines or antibodies of the invention. A suitable source of such proteins is for instance *Streptococcus pneumoniae*. The protein may be used non-purified (associated with in intact cells), partially purified (associated with membrane fragments or other cellular constituents), or purified (i.e. isolated and essentially free of other cellular constituents). Having prepared purified or partially purified one or more of the proteins it is possible to prepare a substantially pure preparation of such a protein. Although numerous methods and strategies for protein purification are known in the art it will be most convenient to purify such a protein by either electrophoresis using for instance a sodium dodecylsulphate-polyacrylamide gel (SDS-PAGE) or by affinity chromatography. Each of these methods will be described below.

A protein encoded by a gene listed in Table 1A-C, 2A-C, 3A-C, and/or 4A-C may be separated from other proteins by electrophoresis using for instance Tricine-SDS-PAGE (Schagger and Von Jagow (1987) Analytical Biochemistry 166, 368-379) or Glycine-SDS-PAGE (Laemmli (1970) Nature 227, 680-685). Other electrophoresis systems that are capable of resolving the various proteins comprised in a bacterial lysate, or transcribed from its genome and expressed in a suitable expression system, may of course also be employed, such as non-denaturing gel electrophoresis. The area of the PAGE gel including the target protein may be excised and the target polypeptides may be eluted therefrom. The protein of interest may be identified by its mobility relative to reference polypeptides in a gel. To increase purity the eluted protein may be run on a second SDS-PAGE gel and eluted a second time. The protein or peptide contained in the excised gel fragment may then be eluted again and is suitable for use in immunization or in protein sequencing.

The protein may also be purified by affinity chromatography using an antibody (such as a monoclonal antibody) that specifically binds to said protein. The antibody may be covalently coupled to solid supports such as celluloses, polystyrene, polyacrylamide, cross-linked dextran, beaded agarose or controlled pore glass using bifunctional coupling agents that react with functional groups on the support and functional groups (i.e., reactive amino acid side chains) on the antibody molecule. Such methods are readily available to the skilled person. The resulting antibody-bearing solid phase is contacted with purified or partially purified protein under reducing conditions using pH, ionic strength, temperature and residence times that permit the protein to bind to the immobilized antibody. The protein is eluted from the column by passing an eluent that dissociates hydrogen bonds through the bed. Buffers at specific pH or NaCl solutions above about 2 M are commonly used eluents.

Methods for carrying out affinity chromatography using antibodies as well as other methods for immunoaffinity purification of proteins are well known in the art (see e.g., Harlow and Lane, (1988) Antibodies: A Laboratory Manual. Cold Spring Harbor Laboratory, Cold Spring Harbor, N.Y.).

With the teachings provided herein, the skilled person is capable of isolating a protein encoded by a gene listed in Table 1, 2, 3 and/or 4 and test it for its immunogenic properties, e.g. by performing an opsonophagocytosis assay as described in WO 01/12219.

Antibody Production

Antibodies, either monoclonal or polyclonal, can be generated to a purified or partially purified protein or peptide fragment encoded by a gene listed in Table 1, 2, 3, and/or 4 in a variety of ways known to those skilled in the art including injection of the protein as an antigen in animals, by hybridoma fusion, and by recombinant methods involving bacteria or phage systems (see Harlow and Lane (1988) supra.; Marks et al., (1992) Journal of Biological Chemistry, 267, 16007-16010; Marks et al., (1992) Biotechnology 10: 779:783; Lowman et al., (1991) Biochem. 30(45): 10832-8; Lerner et al., (1992) Science 258:1313-1314, each of which references discloses suitable methods).

Antibodies against a protein encoded by a gene listed in Table 1, 2, 3, and/or Table 4 or functional homologues thereof, may be produced by immunizing an appropriate vertebrate, preferably mammalian host, e.g., rabbits, goats, rats and mice or chicken with the protein alone or in conjunction with an adjuvant. Usually two or more immunizations will be involved, and the blood or spleen will be harvested a few days after the last injection. For polyclonal antisera, the immunoglobulins may be precipitated, isolated and (affinity) purified. For monoclonal antibodies, the splenocytes will normally be fused with an immortalized lymphocyte, e.g., a myeloid line, under selective conditions for hybridomas. The hybridomas may then be cloned under limiting dilution conditions and their supernatants screened for antibodies having the desired specificity. Techniques for producing (monoclonal) antibodies and methods for their preparation and use in various procedures are well known in the literature (see e.g. U.S. Pat. Nos. 4,381,292, 4,451,570, and 4,618,577; Harlow, E. and Lane, D. (1988) Antibodies: A Laboratory Manual. Cold Spring Harbor Laboratory, Cold Spring Harbor, N.Y.; Ausubel, F. M., Brent, R, Kingston, R E., Moore, D. D., Seidman, J. G., Smith, J. A., Struhl, K. eds. (1998) Current protocols in molecular biology. V. B. Chanda, series ed. New York: John Wiley & Sons; Rose, N., DeMacrio, E., Fahey, J., Friedman, H., Penn, G. (1997) Manual of Clinical Laboratory Immunology. American Soc. Microbiology Press, Washington, D. O Coligan, J. E., Kruisbeek, A. M., Margulies, D. H., Shevach, E. M. Strober, W. (Eds.) (1997) Current Protocols in Immunology. John Wiley & Sons Inc. Baltimore). Typically, an antibody directed against a protein will have a binding affinity of at least $1 \times 10^5 - 1 \times 10^7$ $M^{-1}$.

A recombinant protein or functional homologues thereof, such as may be obtained by expressing a gene from Table 1, 2, 3 and/or 4 in a suitable expression system, is preferred as the antigen in methods for producing an antibody. However, purified proteins may also be used, as well as protein fragments. Antigens suitable for antibody production include any fragment of a protein that elicits an immune response in a mammal exposed to said protein. Preferred antigens of the invention include those fragments that comprise the antigenic determinants, although any region of the proteins encoded by the genes of Tables 1, 2, 3, and/or 4 may in principle be used.

Methods for cloning genomic sequences such as the genes listed in Table 1, 2, 3 and/or 4, for manipulating the genomic sequences to and from expression vectors, and for expressing the protein encoded by the genomic sequence in a heterologous host are well-known, and these techniques can be used to provide the expression vectors, host cells, and the cloned genomic sequences encoding the protein, functional homologues or fragments thereof, which sequences are to be expressed in a host to produce antibodies for use in methods of the present invention (see for instance Sambrook, J., Russell D. W., Sambrook, J. (2001) Molecular Cloning: a Laboratory Manual. Cold Spring Harbor Laboratory Press, Plainview, N.Y., and Ausubel, et al., supra).

A variety of expression systems may be used to produce antigens for use in methods of the present invention. For instance, a variety of expression vectors suitable to produce proteins in Escherichia coli, Lactococcus lactis, Bacillus subtilis, yeast, insect cells, plant cells and mammalian cells have been described, any of which might be used to produce an antigen suitable to be included in a vaccine or useful to produce an antibody or fragment thereof. Of course Streptococcus pneumoniae itself may also be used as an expression vector for this purpose.

One use of antibodies of the invention is to provide active ingredients for a pharmaceutical composition capable of inhibiting virulence or growth of a *Streptococcus pneumoniae* pathogen. Another use of antibodies of the invention is to screen cDNA expression libraries for identifying clones containing cDNA inserts that encode proteins of interest or structurally-related, immuno-cross-reactive proteins. Such screening of cDNA expression libraries is well known in the art (see e.g. Young RA., Davis, R. W. (1983) *Proc. Natl. Acad. Sci. U.S.A.* 80:1194-1198), to which reference is made in this context, as well as other published sources. Another use of these antibodies is for use in affinity chromatography for purification of the protein to which it has been elicited or functional homologues thereof. These antibodies are also useful for assaying for infection with *Streptococcus pneumoniae*.

Antigen Epitopes

The antigen epitopes of this invention, which alone or together form an antigenic determinant of *Streptococcus pneumoniae*, are molecules that are immunoreactive with monoclonal antibodies and whose binding to an antigen of the bacterial pathogen cell prevents the virulence and/or growth of said cell. Systematic techniques for identifying these epitopes are known in the art, as described in U.S. Pat. No. 4,708,871, which is incorporated herein by reference. Typically, these epitopes are short amino acid sequences. These sequences may be embedded in the sequence of longer peptides or proteins, as long as they are accessible.

The epitopes of the invention may be prepared by standard peptide synthesis techniques, such as solid-phase synthesis. Alternatively, the sequences of the invention may be incorporated into larger peptides or proteins by recombinant methods. This is most easily accomplished by preparing a DNA cassette which encodes the sequence of interest, and ligating the cassette into DNA encoding the protein to be modified at the appropriate site. The sequence DNA may be synthesized by standard synthetic techniques, or may be excised from the phage pIII gene using the appropriate restriction enzymes. Epitopes identified herein may be prepared by simple solid-phase techniques. The minimum binding sequence may be determined systematically for each epitope by standard methods, for example, employing the method described in U.S. Pat. No. 4,708,871. Briefly, one may synthesize a set of overlapping oligopeptides derived from an antigen bound to a solid phase array of pins, with a unique oligopeptide on each pin. The pins are arranged to match the format of a 96-well microtiter plate, permitting one to assay all pins simultaneously, e.g., for binding to a monoclonal antibody. Using this method, one may readily determine the binding affinity for every possible subset of consecutive amino acids.

Antibody Formulations and Methods of Administration

The antibodies of this invention are administered at a concentration that is therapeutically effective to prevent or treat infections by *Streptococcus pneumoniae*. To accomplish this goal, the antibodies may be formulated using a variety of acceptable excipients known in the art. Typically, the antibodies are administered by injection, either intravenously or intraperitoneally. Methods to accomplish this administration are known to those of ordinary skill in the art. It may also be possible to obtain compositions which may be topically or orally administered, or which may be capable of transmission across mucous membranes.

Before administration to patients, formulants (components other than the active ingredient in a product that can have many functions, such as carrier and excipients) may be added to the antibodies. A liquid formulation is preferred. For example, these formulants may include oils, polymers, vitamins, carbohydrates, amino acids, salts, buffers, albumin, surfactants, or bulking agents.

Additionally, antibodies can be chemically modified by covalent conjugation to a polymer to increase their circulating half-life, for example. Preferred polymers are polyethylene glycol (PEG) and polyoxyethylated polyols, such as polyoxyethylated sorbitol, polyoxyethylated glucose, polyoxyethylated glycerol (POG). The PEG has a preferred average molecular weight between 1,000 and 40,000, more preferably between 2,000 and 20,000, most preferably between 3,000 and 12,000.

Another drug delivery system for increasing circulatory half-life is the liposome. Methods of preparing liposome delivery systems are discussed in Gabizon et al., Cancer Research (1982) 42:4734; Cafiso, Biochem. Biophys. Acta (1981) 649:129; and Szoka, Ann. Rev. Biophys. Eng. (1980) 9:467. Other drug delivery systems are known in the art and are described in e.g., Poznansky et al., *Drug Delivery Systems* (R. L. Juliano, Ed., Oxford, N.Y. 1980), pp. 253-315; M. L. Poznansky, Pharm. Revs. (1984) 36:277.

After a liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

As stated above, the antibodies and compositions of this invention are used to treat human patients to prevent or treat *Streptococcus pneumoniae* infections. The preferred route of administration is parenterally. In parenteral administration, the compositions of this invention will be formulated in a unit dosage injectable form such as a solution, suspension or emulsion, in association with a pharmaceutically acceptable parenteral vehicle. Such vehicles are inherently nontoxic and nontherapeutic. Examples of such vehicles are saline, Ringer's solution, dextrose solution, and Hanks' solution. Nonaqueous vehicles such as fixed oils and ethyl oleate may also be used. A preferred vehicle is 5% dextrose in saline. The vehicle may contain minor amounts of additives such as substances that enhance isotonicity and chemical stability, including buffers and preservatives. However, also administration routes other than parenteral (e.g. oral, intranasal, rectal, see hereinbelow with regard to vaccine formulations of the invention) can be applicable for certain embodiments of the invention.

The dosage and mode of administration will depend on the individual. Generally, the compositions are administered so that antibodies are given at a dose between 1 µg/kg and 20 mg/kg, more preferably between 20 µg/kg and 10 mg/kg, most preferably between 1 and 7 mg/kg. Preferably, it is given as a bolus dose, to increase circulating levels by 10-20 fold and for 4-6 hours after the bolus dose. Continuous infusion may also be used after the bolus dose. If so, the antibodies may be infused at a dose between 5 and 20 µg/kg/minute, more preferably between 7 and 15 µg/kg/minute.

The antibody of the present invention may be used prior to infection as a precaution, or after infection has occurred as a therapeutic treatment. Preferably, the therapeutic use of the antibodies as described herein or fragments thereof include administration prior or during the acute invasive phase of the disease.

Vaccine Formulations and Methods of Administration

The vaccine antigens of this invention are administered at a concentration that is therapeutically effective to prevent or treat infections by *Streptoccus pneumoniae*. To accomplish this goal, the vaccines may be formulated using a variety of acceptable excipients known in the art. Typically, the vaccines are administered by injection, either intravenously or intraperitoneally. Methods to accomplish this administration are known to those of ordinary skill in the art.

Preferably the vaccine contains at least 50 µg of antigenic mass per dose, and most preferably 80 µg per dose. The antigenic mass being the mass of the antigen protein. Vaccines according to the present invention with an antigenic mass up to 275 µg per dose could even be prepared, and such vaccines may still not elicit local reactions at the injection site. Of course even more micrograms of antigen can be put in a vaccine dose of a vaccine according to the invention, but if the protection obtained with the vaccine is not improved with a higher dose the increase in antigenic load only results in the vaccine being more expensive than necessary. In addition an increasing dose of antigen may eventually lead to unacceptable local reactions at the injection site, which should be avoided.

A vaccine according to the invention may contain a (partially) purified or recombinant protein encoded by a gene listed in Tables 1, 2, 3, and/or 4 or an antigenic part thereof, wherein said recombinant protein is preferably produced by way of expression from a expression vector in suitable host cells, said expression vector containing the gene sequence or an immunogenic part thereof under control of a suitable promoter. Several suitable expression systems are known in the art and may be used in a method to prepare a vaccine according to the invention.

A vaccine according to the invention may further comprise a suitable adjuvant. Many adjuvant systems are known in the art, for example commonly used oil in water adjuvant systems. Any suitable oil may be used, for example a mineral oil known in the art for use in adjuvantia. The oil phase may also contain a suitable mixture of different oils, either mineral or non-mineral. Suitable adjuvantia may also comprise vitamin E, optionally mixed with one or more oils. The water phase of an oil in water adjuvanted vaccine will contain the antigenic material. Suitable formulations will usually comprise from about 25-60% oil phase (40-75% water phase). Examples of suitable formulations may comprise 30% water phase and 70% oil phase or 50% of each. Especially preferred is a non-recombinant lactococcal-based vaccine displaying pneumococcal antigens. The lactococcal-derived bacterial shaped particles are non-living and are designated Gram-positive Enhancer Matrix (GEM) particles (Van Roosmalen, M. L. et al., 2006, Methods 38:144-149). These GEM particles are deprived of surface proteins and the intracellular content is largely degraded (Bosma, T. et al., 2006, Appl. Environ. Microbiol. 72:880-889). The GEM particles can be used as anchoring and delivery vehicle for pneumococcal proteins (see Audouy, S. A. L. et al., 2007, Vaccine 25(13):2497).

The vaccine formulations of the present invention may be used in prophylactic methods of the invention by immunizing a subject by introducing said formulations into said subject subcutaneously, intramuscularly, intranasally, intradermally, intravenously, transdermally, transmucosally, orally, or directly into a lymph node. In another embodiment, the composition may be applied locally, near a local pathogen reservoir against which one would like to vaccinate.

The present invention further provides a method for the manufacture of a vaccine intended for the protection of a subject against pneumococcal infection, wherein said vaccine is combined with a pharmaceutically acceptable diluent, carrier, excipient or adjuvant therefore, such that a formulation is provided which can provide a dose of at least 20 µg protein in a single administration event.

A vaccine (prepared by a method) according to the invention can be used in a method to protect a subject against pneumococcal infection.

To provide adequate protection the vaccine is preferably administered in a 2 shot vaccination regimen, whereby the first shot (priming vaccination) and second shot (boosting vaccination) are given to the subject with a interval of about 3 weeks. In this way the subject will have obtained full protection against pneumococcal infection. The vaccination is very favourable for young children.

A vaccine according to the invention can comprise more than one antigen capable of eliciting antibodies against *Streptococcus pneumoniae*. These antigens can be chosen from the proteins encoded by the genes listed in Table 1, 2, 3, and/or 4, or additionally known antigens, such as those listed in the introduction above may be added.

Further, the genes of Table 1, 2, 3, and/or 4 and/or the proteins encoded by said genes provide excellent targets for small chemical molecules. For finding novel antibiotic compounds a screen with any of these genes and proteins would be suitable.

EXAMPLES

A. Mouse Infection Models

Nine-week old, female outbred CD-1 mice (Harlan, Horst, the Netherlands) were used for all infection models. Aliquots of bacteria stored at −80° C. were rapidly thawed, harvested by centrifugation, and resuspended in sterile PBS to give the required amount of CFU/ml. For the pneumonia model, mice were lightly anaesthetized with 2.5% (v/v) isoflurane/$O_2$, and infected intranasally by pipetting 50 □l of inoculum onto the nostrils of mice held in upright position. At predetermined times after infection, groups of mice were sacrificed by injection anaesthesia, and blood samples were removed by cardiac puncture using a 1 ml syringe. Bacteria were recovered from the nasopharynx by flushing the nostrils with 2 ml sterile PBS (nasopharyngeal lavage, NPL). Bronchoalveolar lung lavage (BAL) was performed by flushing the lungs with 2 ml sterile PBS, after which lungs were removed from the body and homogenized in 2 ml of sterile PBS using a hand held homogeniser. In the colonization model, mice were infected intranasally with 10 □l of inoculum, a volume small enough to only infect the nose (nasopharynx) of the mice. At predetermined time-points after infection, NPL was collected as described above. In the bacteraemia model, mice were infected in a tail vein with a 100 □l inoculum. Bacteria were recovered from the blood by a lateral tail vein puncture from the same mouse at 0, and 12 hours post-infection, and by a cardiac puncture at the last time point, 24 hours post-infection. The number of viable bacteria in NPL, BAL, blood and homogenized lungs was determined by plating serial dilutions on agar plates. All animal experiments were performed with approval of the Radboud University Nijmegen Medical Centre Commitee for Animal Ethics.

B. Genomic Array Footprinting

DNA Isolation. Chromosomal DNA was isolated from pneumococcal cultures by cetyl-trimethylammonium bromide (CTAB) extraction using standard protocols.

Generation of Transposon Mutant Libraries. For in vitro transposon mutagenesis, 1 µg of pneumococcal DNA was incubated in the presence of purified HimarC9 transposase with 0.5 µg of plasmid pR412T7 (Bijlsma, J. J. E. et al., 2007, Appl. Environm. Microbiol. 73(5):1514-1524) as donor for mariner transposon conferring spectinomycin resistance, respectively. After repair of the resulting transposition products with T4 DNA polymerase and *Escherichia coli* DNA ligase, the DNA was used for transformation of strain TIGR4). Preparation and transformation of precompetent *Streptococcus pneumoniae* cell stocks was performed essentially as described. Briefly, cCAT medium was inoculated with several colonies and grown to an optical density at 620 nm ($OD_{620}$) of 0.25-0.3. After a 30-fold dilution of the culture in CTM medium, cells were grown to an $OD_{620}$ of 0.1, pelleted, resuspended in 0.1 volume of CTM-pH7.8 (CTM adjusted to pH 7.8 with NaOH) containing 15% glycerol, and stored at −80° C. For transformation, precompetent TIGR4 cells were grown for 15 minutes at 37° C. in a 10-fold volume of CTM-pH7.8 supplemented with 100 ng/ml CSP-2. After addition of DNA, cultures were incubated for 30 min at 32° C., followed by a two-hour incubation at 37° C. After overnight growth on selective plates containing 150 µg/ml spectinomycin, the required number of colonies were scraped from the plates, pooled, grown to mid-log phase in 20 ml of GM17 medium supplemented with spectinomycin, and stored at −80° C.

Probe Generation, Labeling, and Microarray Hybridization.

Chromosomal DNA from challenged and non-challenged mutant libraries was digested with Alu1 endonuclease. The resulting DNA fragments were purified using Qiagen MinElute columns and used as a template for an in vitro T7 RNA polymerase reaction using the Ambion T7 MegaScript kit. After removal of template DNA by DNAseI treatment, RNA was purified using Qiagen RNeasy MinElute columns. Fluorescent Cy3/Cy5-labeled dUTP nucleotides were incorporated by reverse transcription using Superscript III. Labeled challenged cDNA was mixed with labeled non-challenged cDNA and purified by washing and ultrafiltration using GFX and Microcon-30 spin columns. Samples were suspended in Slidehyb buffer 1 and hybridized in to pneumococcal microarrays for 16 hours at 45° C. Microarrays used in this study were constructed as described and contain amplicons representing 2,087 ORFs of *Streptococcus pneumoniae* TIGR4 and 184 ORFs unique for *Streptococcus pneumoniae* R6, all spotted in duplicate. After hybridization, microarrays were washed with 2×SSC, 0.25% SDS for 5 min, followed by 2 washes in 1×SSC and 0.5×SSC for 5 min each. Finally, slides were dipped into $H_2O$ and dried by centrifugation for 5 min at 50×g.

Microarray Data Analysis. Dual channel array images were acquired on a GenePix 4200AL microarray scanner and analyzed with GenePix Pro software. Spots were screened visually to identify those of low quality and removed from the data set prior to analysis. A net mean intensity filter based on hybridization signals obtained with amplicons representing open reading frames unique for *Streptococcus pneumoniae* strain R6 was applied in all experiments. Slide data were processed and normalized using MicroPreP. Further analysis was performed using a Cyber-T implementation of the Student's t test. This web-based program lists the ratios of all intra-replicates (duplicate spots) and inter-replicates (different slides), the mean ratios per gene, and standard deviations and (Bayesian) p-values assigned to the mean ratios. For identification of conditionally essential genes in the pneumonia model, only genes with a minimum of five reliable measurements, a Bayesian p-value <0.001, a false-discovery rate (FDR) <0.05, and a standard deviation <0.85×abs (ratio) were included. Furthermore, an average fold-change cut-off of 2.5 was applied. For identification of conditionally essential genes in the colonization model, only genes with a minimum of 6 reliable measurements and a Bayesian p-value <0.001 were included. Furthermore, an average fold-change cut-off of 3.0 in a minimum of two time-points, or 5.0 in one time-point was applied.

For identification of conditionally essential genes in the bacteraemia model, only genes with a minimum of five reliable measurements, a Bayesian p-value <0.001, and an average fold-change cut-off of 3.0 were included.

In Silico Analyses. Annotation of genes was derived from the TIGR Comprehensive Microbial Resource database http://cmr.tigr.org/tigr-scripts/CMR/CmrHomePage.cgi).

The computational prediction of subcellular localization of proteins encoded by genes identified in GAF screens was performed using several prediction servers, such as SignalP3.0 (http://www.cbs.dtu.dk/services/SignalP), PSORTb (http://www.psort.org), and TMHMM (http://www.cbs.dtu.dk/services/TMHMM).

C. Experimental Design

To identify genes essential for the pneumococcus in vivo in a murine pneumonia model of infection, three independent *Streptococcus pneumoniae* TIGR4 mariner transposon mutant libraries of different sizes (approximately 100 (M100), 1,000 (M1000), and 10,000 (M10000) CFU), were used to infect groups of six CD-1 mice, e.g., a 50 µl-inoculum containing 1×10$^7$ CFU administered intranasally. Three mice from each group were sacrificed 24 hours after infection, the remaining three 48 hours after infection, at which time-points nasopharyngeal lavage (NPL), bronchoalveolar lavage (BAL), blood, and lungs (homogenized) were collected. Bacterial load in each sample was determined by plating serial dilutions, and the remainder was stored in 15% glycerol at −80° C. Before DNA isolation and GAF, samples were grown in vitro to mid-log phase in GM17 medium supplemented with spectinomycin. GAF analysis of the NPL and blood samples resulted in identification of several mutants that had disappeared from NPL and/or blood during challenge at one or both of the time-points sampled. The corresponding genes can be considered the first potential novel targets identified by in vivo GAF, i.e., *Streptococcus pneumonia* genes essential for nasophayngeal colonization and/or dissemination to and/or survival in the blood in a pneumonia model of infection. These genes are listed in Tables 1A-C and 2A-C.

To identify genes essential for the pneumococcus in vivo specifically during colonization of the nasopharynx, four independent *Streptococcus pneumoniae* TIGR4 mariner transposon mutant libraries of 1,000-2,000 were used to infect groups of sixteen CD-1 mice in a murine colonization model of infection, e.g., a 10 µl-inoculum containing 5×10$^6$ CFU administered intranasally. At four time-points post-infection, namely 0.5, 24, 48, and 96 hours, four mice from each group were sacrificed and nasopharyngeal lavage (NPL) was collected. Bacterial load in each sample was determined by plating serial dilutions, and the remainder was stored in 15% glycerol at −80° C. Before DNA isolation and GAF, samples were grown in vitro to mid-log phase in GM17 medium supplemented with spectinomycin. GAF analysis of the NPL samples resulted in identification of several mutants that had disappeared from NPL during challenge at one or more of the time-points sampled. The corresponding genes can be considered potential novel targets identified by in vivo GAF, i.e., *Streptococcus pneumo-* nia genes essential for nasophayngeal colonization. These genes are listed in Tables 3A-C.

To identify genes essential for the pneumococcus in vivo specifically for survival in the blood stream, a *Streptococcus pneumoniae* TIGR4 mariner transposon mutant library of approximately 1000 CFU was used to infect a group of three CD-1 mice in a murine bacteraemia model of infection, e.g., a 100 µl-inoculum containing 1×10$^6$ CFU administered intravenously. At 24 hours post-infection, the mice were sacrificed and blood was collected. Bacterial load in each sample was determined by plating serial dilutions, and the remainder was stored in 15% glycerol at −80° C. Before DNA isolation and GAF, samples were grown in vitro to mid-log phase in GM17 medium supplemented with spectinomycin. GAF analysis of the blood samples resulted in identification of several mutants that had disappeared from blood during challenge. The corresponding genes can be considered potential novel targets identified by in vivo GAF, i.e., *Streptococcus pneumonia* genes essential for survival in the blood. These genes are listed in Tables 4A-C.

D. Validation of Identified Targets

Construction of Directed Deletion Mutants. A megaprimer PCR method was employed to replace target genes in the genome of the *S. pneumoniae* TIGR4 strain with the spectinomycin-resistance cassette of plasmid pR412T7 (Bijlsma, J. J. E. et al., 2007, Appl. Environm. Microbiol. 73(5):1514-1524; (Burghout, P. et al, 2007, J. Bacteriol. 189(18):6540-6550). In the first step, the spectinomycin resistance cassette and the two flanking regions of the target gene were PCR-amplified using plasmid pR412T7 or chromosomal DNA isolated from TIGR4 as template, respectively. Flanking regions were about 500 bp in length and contained less than 150 bp of the coding sequence of the target gene. For each flanking region, the primer closest to the target gene contained an additional sequence complementary to a spectinomycin-cassette primer. In the second step, the PCR products of the two flanking regions were fused to the spectinomycin-resistance cassette by means of overlap extension PCR, leading to incorporation of the spectinomycin resistance cassette between the two flanking regions of the target gene. The resulting PCR product was transformed into *S. pneumoniae* TIGR4 as described above (Generation of transposon mutant libraries). Transformants were selected on the basis of spectinomycin-resistance and were checked by PCR for recombination at the desired location on the chromosome. Finally, wild-type TIGR4 was transformed with chromosomal DNA isolated from these transformants to rule out the possibility of any additional mutations on the chromosome. A total of 12 deletion mutants were constructed (of genes SP0198, SP0454, SP0514, SP0651, SP0728, SP0749, SP0866, SP1437, SP1492, SP1796, SP2098, and SP2205) which were used in the validation experiments.

Construction of the Streptomycin-Resistant TIGR4 Strain. To obtain the streptomycin-resistant TIGR4::rpsL strain, the rpsL gene encoding a streptomycin-resistant mutant of the ribosomal protein S12 was PCR-amplified from D39::rpsL (Hermans PWM et al., 2006, J. Biol. Chem. 281(2):968-976). This PCR product was introduced into TIGR4 by transformation, and streptomycin-resistant transformants were checked for the rpsL mutations by sequence analysis.

In Vivo Validation: Experimental Setup. To verify the importance of identified genes in pneumococcal infection, their deletion mutants were tested in the mouse pneumonia model in a co-infection setup. Prior to infection, strains were passaged in mice to maintain virulence as described previously (Hendriksen W. T. et al, 2008, J. Bacteriol. 189:1382-1389). For the co-infection, a 50-µl inoculum containing a 1:1 ratio of streptomycin-resistant TIGR4 and a particular mutant (5×10$^6$ CFU total) was used to infect CD-1 mice intranasally as described above (A. MOUSE INFECTION MODELS). This set-up reduces variation between individual mice, inoculation preparation and distribution, and sample collection. Groups of 5 mice were sacrificed 48 hrs post-infection, and nasopharyngeal lavage (NPL), bronchoalveolar lung lavage (BAL), homogenized lungs, and blood were collected. Viable bacteria were quantified by plating serial 10-fold dilutions on blood agar (BA) plates and BA plates supplemented with either streptomycin or trimethoprim. Subsequently, competitive index (CI) scores were calculated for each individual animal as the output ratio of mutant to wild type divided by the input ratio of mutant to wild type bacteria. For experiments in which no mutant bacteria were recovered from a particular mouse, the number 20 (lower limit of detection) was substituted as the numerator. A CI score of 1 indicates equal numbers of wild-type and mutant bacteria, a CI score <1 indicates that the mutant is outcompeted by the wild-type. Comparison of CI scores was performed using the Wilcoxon-signed ranked test (with an arbitrary median of 1) with P<0.05 considered statistically significant.

In Vivo Validation: Results.

Results of the co-infection are shown in FIGS. 2A, 2B and 3. One of the 12 mutants tested, with a deletion of SP2205, showed an attenuated phenotype in all compartments sampled: this mutant was significantly outcompeted by the wild-type in all cases. Six mutants (with deletions in SP0198, SP0454, SP0514, SP0749, SP0866, or SP1437) showed a phenotype in the nasopharynx (NPL) only, while five mutants (with deletions in SP0651, SP0728, SP1492, SP1796, or SP2098) showed no phenotype when tested in the pneumonia co-infection model.

The invention claimed is:

1. A method for prophylactic or therapeutic treatment of a pneumococcal infection in a subject in need thereof, comprising:
   administering to the subject a therapeutically effective amount of a vaccine formulation comprising at least 20 µg of an isolated protein having the amino acid sequence of SEQ ID NO: 1 with at least one of a pharmaceutically acceptable diluent, carrier, excipient or adjuvant therefore.

2. The method of claim 1, wherein the vaccine formulation comprises at least 20 µg and up to 275 µg of the isolated protein having the amino acid sequence of SEQ ID NO: 1.

3. The method of claim 1, wherein the vaccine formulation comprises an oil in water adjuvant system.

4. The method of claim 3, wherein an oil phase of the vaccine formulation comprises an oil selected from the group consisting of mineral oil, a non-mineral oil, and combinations of any thereof.

5. The method of claim 3, wherein the vaccine formulation comprises 40-75% water phase and 25-60% oil phase.

6. The method of claim 4, wherein the vaccine formulation comprises 50% water phase and 50% oil phase.

7. The method of claim 1, where the vaccine formulation comprises vitamin E.

8. The method of claim 1, wherein the pneumococcal infection is an infection by *Streptococcus pneumoniae*.

9. The method of claim 1, wherein the subject is a mammal selected from the group consisting of a human, ape, monkey, horse, cow, pig, goat, dog, cat, rat, mouse, and sheep.

10. The method of claim 9, wherein the subject is a human.

11. The method of claim 1, wherein the isolated protein is partially purified.

12. The method of claim 1, wherein the isolated protein is purified.

13. The method of claim 1, wherein the isolated protein is substantially pure.

14. The method of claim 1, wherein the vaccine formulation is administered by a method selected from the group consisting of subcutaneously, intramuscularly, intranasally, intradermally, intravenously, intraperitoneally, transdermally, transmucosally, orally, directly into a lymph node, and locally.

15. The method of claim 1, wherein the vaccine formulation is administered by injection.

16. The method of claim 1, further comprising administering a boosting vaccine formulation to the subject about 3 weeks after administering the therapeutically effective amount of a vaccine formulation to the subject, wherein the boosting vaccine formulation comprises an isolated protein comprising the amino acid sequence of SEQ ID NO: 1 with at least one of a pharmaceutically acceptable diluent, carrier, excipient or adjuvant therefore.

17. The method of claim 16, wherein the boosting vaccine formulation comprises at least 20 µg and up to 275 µg of the isolated protein having the amino acid sequence of SEQ ID NO: 1.

18. A method for prophylactic or therapeutic treatment of a pneumococcal infection in a subject in need thereof, comprising:
   administering to the subject a therapeutically effective amount of a vaccine formulation comprising a Gram-positive Enhancer Matrix (GEM) particle with at least one of a pharmaceutically acceptable diluent, carrier, excipient or adjuvant therefore, wherein the GEM particle is a non-recombinant lactococcal-derived bacterial shaped particle displaying a protein having the amino acid sequence of SEQ ID NO: 1.

19. The method of claim 18, wherein the vaccine formulation comprises at least 20 µg and up to 275 µg of the protein having the amino acid sequence of SEQ ID NO: 1.

20. The method of claim 18, further comprising administering a boosting vaccine formulation to the subject about 3 weeks after administering the therapeutically effective amount of a vaccine formulation to the subject, wherein the boosting vaccine formulation comprises a Gram-positive Enhancer Matrix (GEM) particle with at least one of a pharmaceutically acceptable diluent, carrier, excipient or adjuvant therefore, and wherein the GEM particle is a non-recombinant lactococcal-derived bacterial shaped particle displaying a protein having the amino acid sequence of SEQ ID NO: 1.

* * * * *